United States Patent
Matsui et al.

(10) Patent No.: US 6,228,600 B1
(45) Date of Patent: *May 8, 2001

(54) IMMUNOASSAYS FOR THE ALPHA PLATELET-DERIVED GROWTH FACTOR RECEPTOR

(75) Inventors: Toshimitsu Matsui, Kita-ku (JP); Stuart A. Aaronson, New York, NY (US); Jacalyn H. Pierce, Pukalani, HI (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/460,656

(22) Filed: Jun. 2, 1995

Related U.S. Application Data

(62) Division of application No. 08/439,095, filed on May 11, 1995, which is a continuation of application No. 07/915,884, filed on Jul. 20, 1992, now abandoned, which is a continuation of application No. 07/308,282, filed on Feb. 9, 1998, now abandoned.

(51) Int. Cl.$^7$ .................. G01N 33/53; G01N 33/577; C07K 16/28

(52) U.S. Cl. ............... 435/7.21; 435/7.2; 435/7.24; 435/7.4; 435/21; 436/518; 436/536; 436/548; 530/387.9; 530/388.22; 530/389.6

(58) Field of Search ................ 435/7.2, 7.21, 435/7.24, 7.4, 21; 530/387.9, 388.22, 388.26, 389.6, 391.3; 436/518, 536, 548

(56) References Cited

U.S. PATENT DOCUMENTS

| | | |
|---|---|---|
| 4,766,073 | 8/1988 | Murray et al. . |
| 5,094,941 | 3/1992 | Hart . |
| 5,100,774 | 3/1992 | Rakowicz-Szulczynska . |
| 5,219,727 | 6/1993 | Wang et al. . |
| 5,371,205 | 12/1994 | Kelly et al. . |
| 5,468,468 | 11/1995 | LaRochelle et al. ........... 530/388.22 |
| 5,863,739 * | 1/1999 | LaRochelle et al. ................ 435/7.2 |
| 6,043,211 | 3/2000 | Williams et al. . |
| 6,110,737 | 8/2000 | Escobedo et al. . |

FOREIGN PATENT DOCUMENTS 327 369    8/1989  (EP) .

OTHER PUBLICATIONS

Claesson–Welsh et al., 1987. Biosynthesis and intracellular transport of the receptor for platelet–derived growth factor. Proc. Natl. Acad. Sci. 84: 8796–8800.

Claesson–Welsh et al., Jan. 1989. Identification and structural analysis of the A type receptor for platelet–derived growth factor. J. Biol. Chem. 264: 1742–1747.

Escobedo et al., Jan. 1988. Platelet–derived growth factor receptors expressed by cDNA transfection couple to a diverse group of cellular responses associated with cell proliferation. J. Biol. Chem. 263: 1482–1487.

Bishayee et al., 1988. Characterization of a novel anti–peptide antibody that recognizes a specific conformation of the platelet–derived growth factor receptor. Mol. Cell. Biol. 8: 3696–3702.

Keating et al., 1988. Ligand activation causes a phosphorylation–dependent change in platelet–derived growth factor receptor conformation. J. Biol. Chem. 263: 12805–12808.

Heldin et al., May 1988. Binding of different dimeric forms of PDGF to human fibroblasts: evidence for two separate receptor types. EMBO J. 7(5): 1387–1393.

Hart et al., 1987. Synthesis, phosphorylation, and degradation of multiple forms of the platelet–derived growth factor receptor studied using a monoclonal antibody. J. Biological Chem. 262(22): 10780–10785.

Frackelton et al., 1984. Evidence for the platelet–derived growth factor–stimulated tyrosine phosphorylation of the platelet–derived growth factor receptor in vivo. J. Biological Chem. 259(12): 7909–7915.

Kawahara et al., "Monoclonal Antibody C3.1 is a Platelet Derived Growth Factor (PDGF) Antagonist," *Biochem. Biophys. Res. Comm.*, 147(2); 839–845 (1987).

Nister et al., "Expression of Messenger RNAs for Platelet–derived Growth Factor and Transforming Growth Factor–α and Their Receptors in Human Malignant Glioma Cell Lines," *Can. Res.*, 48: 3910–3918 (1988).

Escobedo et al., A common PDGF Receptor is Activated by Homodimeric A and B Forms of PDGF, *Science*, 240: 1532–1534 (1998).

Johnsson, Platelet–Derived Growth Factor: Identification of Constituent Polypeptide Chains, *Biochem. Biophys. Res. Comm.*, 104(1): 66–74 (1982).

Gronwald et al., Cloning and Expression of a cDNA Coding for the Human Platelet–Derived Growth Factor Receptor: Evidence For More Than One Receptor Class, *Proc. Natl. Acad. Sci. USA*, 85: 3435–3439 (1988).

Betsholtz et al., "Coexpression of a PDGF–Like Growth Factor and PDGF Receptors in a Human Osteosarcoma Cell Line: Implications for Autocrine Activation" *Cell*, 39: 447–457 (1984).

Matsui et al., "Isolation of A Novel Receptor cDNA Establishes the Existence of Two PDGF Receptor Genes" *Science*, 243: 800–804, (1989).

(List continued on next page.)

*Primary Examiner*—Long V. Le
*Assistant Examiner*—James L. Grun
(74) *Attorney, Agent, or Firm*—Needle & Rosenberg, P.C.

(57) ABSTRACT

Recombinant DNA technology was used to clone encoding nucleic acids for the human alpha platelet-derived growth factor receptor (PDGF-R type alpha). Peptides corresponding to the predicted sequence of this type and of the PDGF-R type beta were used to elicit antibodies specific for either type of the PDGF-R. Immunoassays are described for determining the level of PDGF-R type alpha in biological samples with the PDGF-R type alpha-specific antibodies.

3 Claims, 27 Drawing Sheets

OTHER PUBLICATIONS

Miki et al., "An Efficient Directional Cloning System to Construct cDNA Libraries Containing Full–Length Inserts at High Frequency" *Gene*, 83(1) : 137–146 (1989).

Giese et al., The Role of Individual Cysteine Residues in the Structure and Function of the v–esis Gene Product, *Science*, 236: 1315–1318 (1987).

Hart et al., "Two Classes of PDGF Receptor Recognize Different Isofoms of PDGF" *Science*, 240: 1529–1531 (1988).

Claesson–Welsh et al., cDNA Cloning and Expression of a Human Platelet–Derived Growth Factor (PDGF) Receptor Specific for β–type Chain PDGF Molecules, a *Mol. Cell, Biol*, 8(8): 3476–3486 (1988).

Kruh et al., "A Novel Gene Closely Related to the abl proto–Oncogene", *Science*, 234: 1545–1548 (1986).

King et al., "Amplification of A Novel v–erbB–Related Gene in a Human Mammary Carcinoma", *Sicnece*, 229: 974–976 (1985).

Claesson–Welsh et al., "cDNA Cloning and Expression of a Human A–Type Platelet–Derived Growth Factor (PDGF) Receptor Establishes Structural Similarity to the B–Type PDGF Receptor," *PNAS*, (USA), 86(13): 4917–4921 (1989).

Yarden et al., "Structure of the Receptor For Platelet–Derived Growth Factor Helps Define A Family Of Closely Related Growth Factor Receptors", *Nature*, vol. 323:226–32, (1986).

* cited by examiner

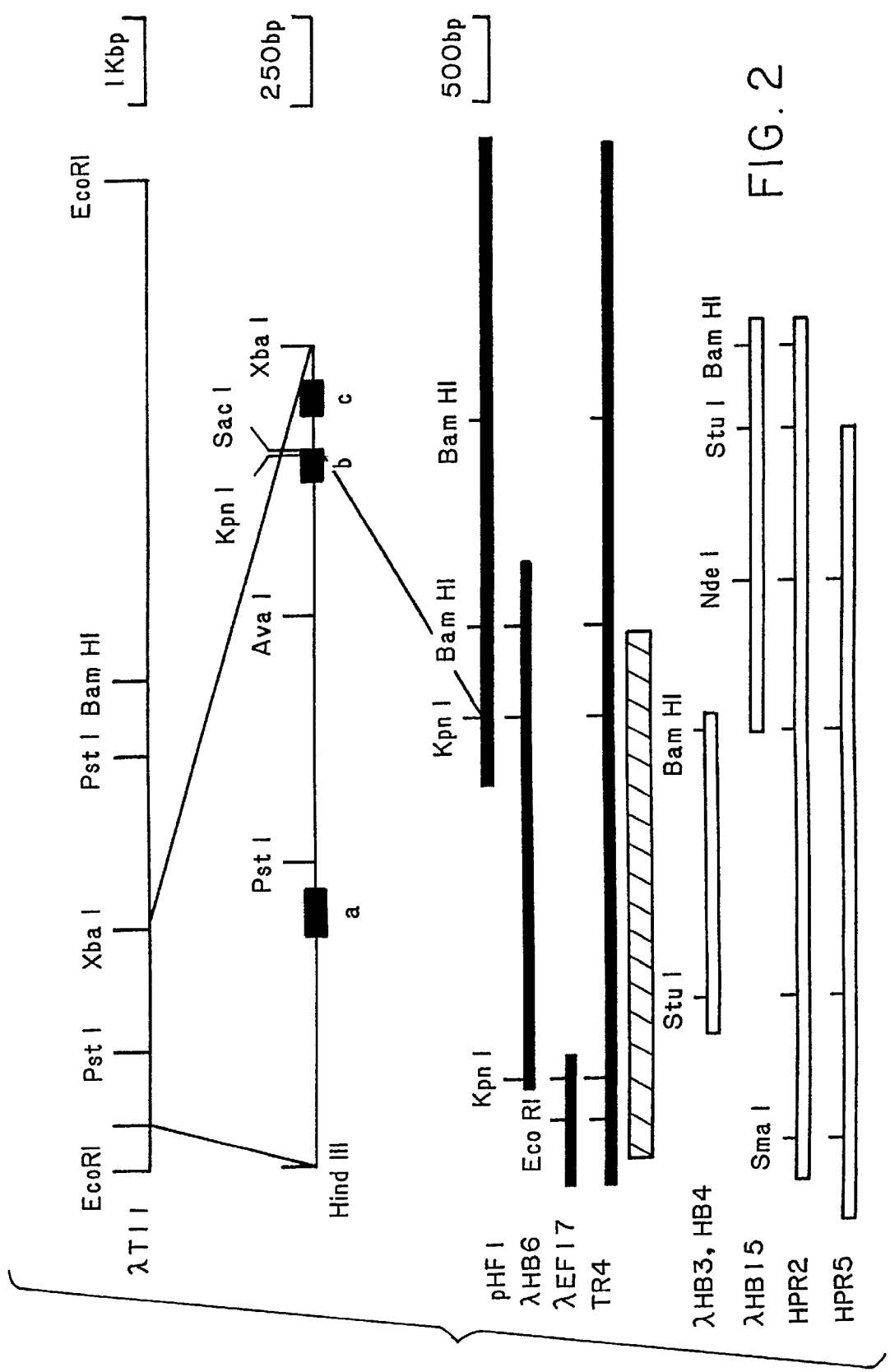

FIG. 3-1

```
  1 CCATTACTGTTGGAGCTACAGGGAGAGAAACAGGAGGAGACTGCAAGAGA

49 TCATTTGGGAAGGCCGTGGGCACGCTCTTTACTCCATGTGTGGGACATT

MetGly
100 CATTGCGGAATAACATCGGAGGAGAAGTTTCCCAGAGCTATGGGG 5              10             15
       ThrSerHisProAlaPheLeuValLeuGlyCysLeuLeuThrGly
145 ACTTCCCATCCGGCGTTCCTGGTCTTAGGCTGTCTTCTCACAGG 20             25             30
       LeuSerLeuIleLeuCysGlnLeuSerLeuProSerIleLeuPro
190 CTGAGCCTAATCCTCTGCCAGCTTTCATTACCCTCTATCCTTCCA 35             40             45
       AsnGluAsnGluLysValValGlnLeuAsnSerSerPheSerLeu
235 AATGAAAATGAAAAGGTTGTGCAGCTGAATTCATCCTTTTCTCTG 50             55             60
       ArgCysPheGlyGluSerGluValSerTrpGlnTyrProMetSer
280 AGATGCTTTGGGGAGAGTGAAGTGAGCTGGCAGTACCCCATGTCT 65             70             75
       GluGluGluSerSerAspValGluIleArgAsnGluGluAsnAsn
325 GAAGAAGAGAGCTCCGATGTGGAAATCAGAAATGAAGAAAACAAC 80             85             90
       SerGlyLeuPheValThrValLeuGluValSerSerAlaSerAla
370 AGCGGCCTTTTTGTGACGGTCTTGGAAGTGAGCAGTGCCTCGGCG 95            100            105
       AlaHisThrGlyLeuTyrThrCysTyrTyrAsnHisThrGlnThr
415 GCCCACACAGGGTTGTACACTTGCTATTACAACCACACTCAGACA 110            115            120
       GluGluAsnGluLeuGluGlyArgHisIleTyrIleTyrValPro
460 GAAGAGAATGAGCTTGAAGGCAGGCACATTTACATCTATGTGCCA 125            130            135
       AspProAspValAlaPheValProLeuGlyMetThrAspTyrLeu
505 GACCCAGATGTAGCCTTTGTACCTCTAGGAATGACGGATTATTTA
```

FIG. 3-2

```
                    140                 145                  150
         ValIleValGluAspAspAspSerAlaIleIleProCysArgThr
550      GTCATCGTGGAGGATGATGATTCTGCCATTATACCTTGTCGCACA 155                 160                  165
         ThrAspProGluThrProValThrLeuHisAsnSerGluGlyVal
595      ACTGATCCCGAGACTCCTGTAACCTTACACAACAGTGAGGGGGTG 170                 175                  180
         ValProAlaSerTyrAspSerArgGlnGlyPheAsnGlyThrPhe
640      GTACCTGCCTCCTACGACAGCAGACAGGGCTTTAATGGGACCTTC 185                 190                  195
         ThrValGlyProTyrIleCysGluAlaThrValLysGlyLysLys
685      ACTGTAGGGCCCTATATCTGTGAGGCCACCGTCAAAGGAAAGAAG 200                 205                  210
         PheGlnThrIleProPheAsnValTyrAlaLeuLysAlaThrSer
730      TTCCAGACCATCCCATTTAATGTTTATGCTTTAAAAGCAACATCA 215                 220                  225
         GluLeuAspLeuGluMetGluAlaLeuLysThrValTyrLysSer
775      GAGCTGGATCTAGAAATGGAAGCTCTTAAAACCGTGTATAAGTCA 230                 235                  240
         GlyGluThrIleValValThrCysAlaValPheAsnAsnGluVal
820      GGGGAAACGATTGTGGTCACCTGTGCTGTTTTTAACAATGAGGTG 245                 250                  255
         ValAspLeuGlnTrpThrTyrProGlyGluValLysGlyLysGly
865      GTTGACCTTCAATGGACTTACCCTGGAGAAGTGAAAGGCAAAGGC 260                 265                  270
         IleThrMetLeuGluGluIleLysValProSerIleLysLeuVal
910      ATCACAATGCTGGAAGAAATCAAAGTCCCATCCATCAAATTGGTG 275                 280                  285
         TyrThrLeuThrValProGluAlaThrValLysAspSerGlyAsp
955      TACACTTTGACGGTCCCCGAGGCCACGGTGAAAGACAGTGGAGAT 290                 295                  300
         TyrGluCysAlaAlaArgGlnAlaThrArgGluValLysGluMet
1000     TACGAATGTGCTGCCCGCCAGGCTACCAGGGAGGTCAAAGAAATG 305                 310                  315
         LysLysValThrIleSerValHisGluLysGlyPheIleGluIle
1045     AAGAAAGTCACTATTTCTGTCCATGAGAAGGTTTCATTGAAATC
```

FIG. 3-3

```
              320              325               330
      LysProThrPheSerGlnLeuGluAlaValAsnLeuHisGluVal
1090  AAACCCACCTTCAGCCAGTTGGAAGCTGTCAACCTGCATGAAGTC 335              340               345
      LysHisPheValValGluValArgAlaTyrProProProArgIle
1135  AAACATTTTGTTGTAGAGGTGCGGGCCTACCCACCTCCCAGGATA 350              355               360
      SerTrpLeuLysAsnAsnLeuThrLeuIleGluAsnLeuThrGlu
1180  TCCTGGCTGAAAAACAATCTGACTCTGATTGAAAATCTCACTGAG 365              370               375
      IleThrThrAspValGluLysIleGlnGluIleArgTyrArgSer
1225  ATCACCACTGATGTGGAAAAGATTCAGGAAATAAGGTATCGAAGC 380              385               390
      LysLeuLysLeuIleArgAlaLysGluGluAspSerGlyHisTyr
1270  AAATTAAAGCTGATCCGTGCTAAGGAAGAAGACAGTGGCCATTAT 395              400               405
      ThrIleValAlaGlnAsnGluAspAlaValLysSerTyrThrPhe
1315  ACTATTGTAGCTCAAAATGAAGATGCTGTGAAGAGCTATACTTTT 410              415               420
      GluLeuLeuThrGlnValProSerSerIleLeuAspLeuValAsp
1360  GAACTGTTAACTCAAGTTCCTTCATCCATTCTGGACTTGGTCGAT 425              430               435
      AspHisHisGlySerThrGlyGlyGlnThrValArgCysThrAla
1405  GATCACCATGGCTCAACTGGGGGACAGACGGTGAGGTGCACAGCT 440              445               450
      GluGlyThrProLeuProAspIleGluTrpMetIleCysLysAsp
1450  GAAGGCACGCCGCTTCCTGATATTGAGTGGATGATATGCAAAGAT 455              460               465
      IleLysLysCysAsnAsnGluThrSerTrpThrIleLeuAlaAsn
1495  ATTAAGAAATGTAATAATGAAACTTCCTGGACTATTTTGGCCAAC 470              475               480
      AsnValSerAsnIleIleThrGluIleHisSerArgAspArgSer
1540  AATGTCTCAAACATCATCACGGAGATCCACTCCCGAGACAGGAGT 485              490               495
      ThrValGluGlyArgValThrPheAlaLysValGluGluThrIle
1585  ACCGTGGAGGGCCGTGTGACTTTCGCCAAAGTGGAGGAGACCATC
```

FIG. 3-4

```
                500               505                510
       AlaValArg[Cys]LeuAlaLysAsnLeuLeuGlyAlaGluAsnArg
1630   GCCGTGCGATGCCTGGCTAAGAATCTCCTTGGAGCTGAGAACCGA 515               520                525
       GluLeuLysLeuValAlaProThrLeuArgSerGluLeuThrVal
1675   GAGCTGAAGCTGGTGGCTCCCACCCTGCGTTCTGAACTCACGGTG 530               535                540
       AlaAlaAlaValLeuValLeuLeuValIleValIleIleSerLeu
1720   GCTGCTGCAGTCCTGGTGCTGTTGGTGATTGTGATCATCTCACTT 545               550                555
       IleValLeuValValIleTrpLysGlnLysProArgTyrGluIle
1765   ATTGTCCTGGTTGTCATTTGGAAACAGAAACCGAGGTATGAAATT 560               565                570
       ArgTrpArgValIleGluSerIleSerProAspGlyHisGluTyr
1810   CGCTGGAGGGTCATTGAATCAATCAGCCCGGATGGACATGAATAT 575               580                585
       IleTyrValAspProMetGlnLeuProTyrAspSerArgTrpGlu
1855   ATTTATGTGGACCCGATGCAGCTGCCTTATGACTCAAGATGGGAG 590               595                600
       PheProArgAspGlyLeuValLeuGlyArgValLeuGlySerGly
1900   TTTCCAAGAGATGGACTAGTGCTTGGTCGGGTCTTGGGGTCTGGA 605               610                615
       AlaPheGlyLysValValGluGlyThrAlaTyrGlyLeuSerArg
1945   GCGTTTGGGAAGGTGGTTGAAGGAACAGCCTATGGATTAAGCCGG 620               625                630
       SerGlnProValMetLysValAlaValLysMetLeuLysProThr
1990   TCCCAACCTGTCATGAAAGTTGCAGTGAAGATGCTAAAACCCACG 635               640                645
       AlaArgSerSerGluLysGlnAlaLeuMetSerGluLeuLysIle
2035   GCCAGATCCAGTGAAAAACAAGCTCTCATGTCTGAACTGAAGATA 650               655                660
       MetThrHisLeuGlyProHisLeuAsnIleValAsnLeuLeuGly
2080   ATGACTCACCTGGGGCCACATTTGAACATTGTAAACTTGCTGGGA 665               670                675
       Ala[Cys]ThrLysSerGlyProIleTyrIleIleThrGluTyr[Cys]·
2125   GCCTGCACCAAGTCAGGCCCCATTTACATCATCACAGAGTATTGC
```

FIG. 3-5

```
              680                685                690
       PheTyrGlyAspLeuValAsnTyrLeuHisLysAsnArgAspSer
2170   TTCTATGGAGATTTGGTCAACTATTTGCATAAGAATAGGGATAGC 695                700                705
       PheLeuSerHisHisProGluLysProLysLysGluLeuAspIle
2215   TTCCTGAGCCACCACCCAGAGAAGCCAAAGAAAGAGCTGGATATC 710                715                720
       PheGlyLeuAsnProAlaAspGluSerThrArgSerTyrValIle
2260   TTTGGATTGAACCCTGCTGATGAAAGCACACGGAGCTATGTTATT 725                730                735
       LeuSerPheGluAsnAsnGlyAspTyrMetAspMetLysGlnAla
2305   TTATCTTTTGAAAACAATGGTGACTACATGGACATGAAGCAGGCT 740                745                750
       AspThrThrGlnTyrValProMetLeuGluArgLysGluValSer
2350   GATACTACACAGTATGTCCCCATGCTAGAAAGGAAAGAGGTTTCT 755                760                765
       LysTyrSerAspIleGlnArgSerLeuTyrAspArgProAlaSer
2395   AAATATTCCGACATCCAGAGATCACTCTATGATCGTCCAGCCTCA 770                775                780
       TyrLysLysLysSerMetLeuAspSerGluValLysAsnLeuLeu
2440   TATAAGAAGAAATCTATGTTAGACTCAGAAGTCAAAAACCTCCTT 785                790                795
       SerAspAspAsnSerGluGlyLeuThrLeuLeuAspLeuLeuSer
2485   TCAGATGATAACTCAGAAGGCCTTACTTTATTGGATTTGTTGAGC 800                805                810
       PheThrTyrGlnValAlaArgGlyMetGluPheLeuAlaSerLys
2530   TTCACCTATCAAGTTGCCCGAGGAATGGAGTTTTTGGCTTCAAAA 815                820                825
       Asn[Cys]ValHisArgAspLeuAlaAlaArgAsnValLeuLeuAla
2575   AATTGTGTCCACCGTGATCTGGCTGCTCGAACGTCCTCCTGGCA 830                835                840
       GlnGlyLysIleValLysIleCysAspPheGlyLeuAlaArgAsp
2620   CAAGGAAAAATTGTGAAGATCTGTGACTTTGGCCTGGCCAGAGAC 845                850                855
       IleMetHisAspSerAsnTyrValSerLysGlySerThrPheLeu
2665   ATCATGCATGATTCGAACTATGTGTCGAAAGGCAGTACCTTTCTG
```

FIG. 3-6

```
            860              865              870
     ProValLysTrpMetAlaProGluSerIlePheAspAsnLeuTyr
2710 CCCGTGAAGTGGATGGCTCCTGAGAGCATCTTTGACAACCTCTAC
                          | a |

875              880              885
     ThrThrLeuSerAspValTrpSerTyrGlyIleLeuLeuTrpGlu
2755 ACCACACTGAGTGATGTCTGGTCTTATGGCATTCTGCTCTGGGAG 890              895              900
     IlePheSerLeuGlyGlyThrProTyrProGlyMetMetValAsp
2800 ATCTTTTCCCTTGGTGGCACCCCTTACCCCGGCATGATGGTGGAT
                     /\

905              910              915
     SerThrPheTyrAsnLysIleLysSerGlyTyrArgMetAlaLys
2845 TCTACTTTCTACAATAAGATCAAGAGTGGGTACCGGATGGCCAAG
     | b |

920              925              930
     ProAspHisAlaThrSerGluValTyrGluIleMetValLysCys
2890 CCTGACCACGCTACCAGTGAAGTCTACGAGATCATGGTGAAATGC
                                /\

935              940              945
     TrpAsnSerGluProGluLysArgProSerPheTyrHisLeuSer
2935 TGGAACAGTGAGCCGGAGAAGAGACCCTCCTTTTACCACCTGAGT
                          | c |

950              955              960
     GluIleValGluAsnLeuLeuProGlyGlnTyrLysLysSerTyr
2980 GAGATTGTGGAGAATCTGCTGCCTGGACAATATAAAAAGAGTTAT
                                          /

965              970              975
     GluLysIleHisLeuAspPheLeuLysSerAspHisProAlaVal
3025 GAAAAAATTCACCTGGACTTCCTGAAGAGTGACCATCCTGCTGTG 980              985              990
     AlaArgMetArgValAspSerAspAsnAlaTyrIleGlyValThr
3070 GCACGCATGCGTGTGGACTCAGACAATGCATACATTGGTGTCACC 995              1000             1005
     TyrLysAsnGluGluAspLysLeuLysAspTrpGluGlyGlyLeu
3115 TACAAAAACGAGGAAGACAAGCTGAAGGACTGGGAGGGTGGTCTG
```

FIG. 3-7

```
                1010              1015              1020
       AspGluGlnArgLeuSerAlaAspSerGlyTyrIleIleProLeu
3160   GATGAGCAGAGACTGAGCGCTGACAGTGGCTACATCATTCCTCTG 1025              1030              1035
       ProAspIleAspProValProGluGluGluAspLeuGlyLysArg
3205   CCTGACATTGACCCTGTCCCTGAGGAGGAGGACCTGGGCAAGAGG 1040              1045              1050
       AsnArgHisSerSerGlnThrSerGluGluSerAlaIleGluThr
3250   AACAGACACAGCTCGCAGACCTCTGAAGAGAGTGCCATTGAGACG 1055              1060              1065
       GlySerSerSerSerThrPheIleLysArgGluAspGluThrIle
3295   GGTTCCAGCAGTTCCACCTTCATCAAGAGAGAGGACGAGACCATT 1070              1075              1080
       GluAspIleAspMetMetAspAspIleGlyIleAspSerSerAsp
3340   GAAGACATCGACATGATGGACGACATCGGCATAGACTCTTCAGAC

1085
       LeuValGluAspSerPheLeu
3385   CTGGTGGAAGACAGCTTCCTGTAACTGGCGGATTCGAGGGGTTCC

3430   TTCCACTTCTGGGGCCACCTCTGGATCCCGTTCAGAAAACCACTT

3475   TATTGCAATGCGGAGGTTGAGAGGAGGACTTGGTTGATGTTTAAA

3520   GAGAAGTTCCCAGCCAAGGGCCTCGGGGAGCGTTCTAAATATGAA

3565   TGAATGGGATATTTTGAAATGAACTTTGTCAGTGTTGCCTCTCGC

3610   AATGCCTCAGTAGCATCTCAGTGGTGTGTGAAGTTTGGAGATAGA

3655   TGGATAAGGGAATAATAGGCCACAGAAGGTGAACTTTGTGCTTCA

3700   AGGACATTGGTGAGAGTCCAACAGACACAATTTATACTGCGACAG

3745   AACTTCAGCATTGTAATTATGTAAATAACTCTAACCAAGGCTGTG

3790   TTTAGATTGTATTAACTATCTTCTTTGGACTTCTGAAGAGACCAC

3835   TCAATCCATCCATGTACTTCCCTCTTGAAACCTGATGTCAGCTGC

3880   TGTTGAACTTTTTAAAGAAGTGCATGAAAAACCATTTTTGAACCT

3925   TAAAAGGTACTGGTACTATAGCATTTTGCTATCTTTTTTAGTGTT
```

FIG. 3-8

```
3970 AAGAGATAAAGAATAATAATTAACCAACCTTGTTTAATAGATTTG
4015 GGTCATTTAGAAGCCTGACAACTCATTTTCATATTGTAATCTATG
4060 TTTATAATACTACTGTTATCAGTAATGCTAAATGTGTAATAA
4105 TGTAACATGATTTCCCTCCAGAGAAGCACAATTTAAAACAATCC
4150 TTACTAAGTAGGTGATGAGTTTGACAGTTTTTGACATTTATATTA
4195 AATAACATGTTTCTCTATAAAGTATGGTAATAGCTTTAGTGAATT
4240 AAATTTAGTTGAGCATAGAGAACAAAGTAAAAGTAGTGTTGTCCA
4285 GGAAGTCAGAATTTTTAACTGTACTGAATAGGTTCCCCAATCCAT
4330 CGTATTAAAAAACAATTAACTGCCCTCTGAAATAATGGGATTAGA
4375 AACAAACAAAACTCTTAAGTCCTAAAAGTTCTCAATGTAGAGGCA
4420 TAAACCTGTGCTGAACATAACTTCTCATGTATATTACCCAATGGA
4465 AAATATAATGATCAGCAAAAAGACTGGATTTGCAGAAGTTTTTTT
4510 TTTTTTTCTTCATGCCTGATGAAAGCTTTGGCAACCCCAATATAT
4555 GTATTTTTTGAATCTATGAACCTGAAAAGGGTCAGAAGGATGCCC
4600 AGACATCAGCCTCCTTCTTTCACCCCTTACCCCAAAGAGAAAGAG
4645 TTTGAAACTCGAGACCATAAAGATATTCTTTAGTGGAGGCTGGAT
4690 GTGCATTAGCCTGGATCCTCAGTTCTCAAATGTGTGTGGCAGCCA
4735 GGATGACTAGATCCTGGGTTTCCATCCTTGAGATTCTGAAGTATG
4780 AAGTCTGAGGGAAACCAGAGTCTGTATTTTTCTAAACTCCCTGGC
4825 TGTTCTGATCGGCCAGTTTTCGGAAACACTGACTTAGGTTTCAGG
4870 AAGTTGCCATGGGAAACAAATAATTTGAACTTTGGAACAGGGTTG
4915 GAATTCAACCACGCAGGAAGCCTACTATTTAAATCCTTGGCTTCA
4960 GGTTAGTGACATTTAATGCCATCTAGCTAGCAATTGCGACCTTAA
5005 TTTAACTTTCCAGTCTTAGCTGAGGCTGAGAAAGCTAAAGTTTGG
```

FIG. 3-9

```
5050  TTTTGACAGGTTTTCCAAAAGTAAAGATGCTACTTCCCACTGTAT
5095  GGGGGAGATTGAACTTTCCCCGTCTCCCGTCTTCTGCCTCCCACT
5140  CCATACCCCGCCAAGGAAAGGCATGTACAAAAATTATGCAATTCA
5185  GTGTTCCAAGTCTCTGTGTAACCAGCTCAGTGTTTTGGTGGAAAA
5230  AACATTTTAAGTTTTACTGATAATTTGAGGTTAGATGGGAGGATG
5275  AATTGTCACATCTATCCACACTGTCAAACAGGTTGGTGTGGGTTC
5320  ATTGGCATTCTTTGCAATACTGCTTAATTGCTGATACCATATGAA
5365  TGAAACATGGGCTGTGATTACTGCAATCACTGTGCTATCGGCAGA
5410  TGATGCTTTGGAAGATGCAGAAGCAATAATAAAGTACTTGACTAC
5455  CTACTGGTGTAATCTCAATGCAAGCCCCAACTTTCTTATCCAACT
5500  TTTTCATAGTAAGTGCGAAGACTGAGCCAGATTGGCCAATTAAAA
5545  ACGAAAACCTGACTAGGTTCTGTAGAGCCAATTAGACTTGAAATA
5590  CGTTTGTGTTTCTAGAATCACAGCTCAAGCATTCTGTTTATCGCT
5635  CACTCTCCCTTGTACAGCCTTATTTTGTTGGTGCTTTGCATTTTG
5680  ATATTGCTGTGAGCCTTGCATGACATCATGAGGCCGGATGAAACT
5725  TCTCAGTCCAGCAGTTTCCAGTCCTAACAAATGCTCCCACCTGAA
5770  TTTGTATATGACTGCATTTGTGGGTGTGTGTGTTTTCAGCAAA
5815  TTCCAGATTTGTTTCCTTTTGGCCTCCTGCAAAGTCTCCAGAAGA
5860  AAATTTGCCAATCTTTCCTACTTTCTATTTTTATGATGACAATCA
5905  AAGCCGGCCTGAGAAACACTATTTGTGACTTTTTAAACGATTAGT
5950  GATGTCCTTAAAATGTGGTCTGCCAATCTGTACAAAATGGTCCTA
5995  TTTTTGTGAAGAGGGACATAAGATAAAATGATGTTATACATCAAT
6040  ATGTATATATGTATTTCTATATAGACTTGGAGAATACTGCCAAAA
6085  CATTTATGACAAGCTGTATCACTGCCTTCGTTTATATTTTTTTAA
```

```
6130    CTGTGATAATCCCCACAGGCACATTAACTGTTGCACTTTTGAATG

6175    TCCAAAATTTATATTTTAGAAATAATAAAAAGAAAGATACTTACA

6220    TGTTCCCAAAACAATGGTGTGGTGAATGTGTGAGAAAAACTAACT

6265    TGATAGGGTCTACCAATACAAAATGTATTACGAATGCCCCTGTTC

6310    ATGTTTTTGTTTTAAAACGTGTAAATGAAGATCTTTATATTTCAA

6355    TAAATGATATATAATTTAAAGTTAAAAAAAAAAAAAAAAAAAAAA

6400    AAAAAAAAAAAA
```

FIG. 3-10

IMMUNOASSAYS FOR THE ALPHA PLATELET-DERIVED GROWTH FACTOR RECEPTOR

This application is a divisional of application Ser. No. 08/439,095, fled on May 11, 1995, pending, which is a continuation of Ser. No. 07/915,884,, filed on Jul. 20, 1992, now abandoned, which is a continuation of Ser. No. 07/308, 282, filed on Feb. 9, 1989, now abandoned.

FIELD OF THE INVENTION

The present invention relates to genes which encode receptor proteins for Platelet-Derived Growth Factor (PDGF), particularly to those human genes encoding receptor proteins which preferentially bind the major form of human PDGF which is found in platelets. This invention also relates to synthesis of products of such PDGF receptor genes by recombinant cells, and to the manufacture and use of certain other novel products enabled by the identification and cloning of DNAs encoding these receptors.

BACKGROUND OF THE INVENTION

Genes encoding growth factors and their receptors have been implicated in the regulation of normal cell growth and development. There is also increasing evidence that genetic alterations affecting expression of such genes can contribute to altered cell growth associated with malignancy. The normal homologues of some oncogenes code for membrane-spanning growth factor receptors with tyrosine kinase activity (2, 3). Other oncogenes appear to act in pathways of growth factor activated cell proliferation as well (4). Thus, increased knowledge of growth factor regulatory systems in general is expected to provide better understanding of genes critically involved in both normal growth control and neoplasia.

Platelet-Derived Growth Factor (PDGF) is of particular importance because it is a major connective tissue cell mitogen which is thought to play a major role in normal wound healing. Further, the abnormal expression of PDGF has been implicated not only in cancers, but also in a variety of histopathologic states including arteriosclerosis, arthritis, and fibrotic diseases (23).

PDGF consists of a disulfide-linked dimer of two polypeptide chains, designated A and B. There is evidence for the natural occurrence of all three possible dimeric structures containing A or B chains or both (1, 25, 26). The various dimeric forms of the growth factor are called "isoforms". A variety of normal and neoplastic cells appear to specifically express either the A or B chains. Nevertheless, the most significant human isoform for physiological regulatory processes is believed to be the one isolated from human platelets, namely the AB heterodimer (i.e., a dimer containing one A and one B chain; see reference 24).

The PDGF-A and B chains have distinguishable properties (37). The A chain is much more efficiently secreted and exhibits lower specific mitogenic activity than the B chain. The B chain gene of PDGF has been shown to be the normal human homologue of the simian sarcoma virus-derived v-sis oncogene. Moreover, there is accumulating evidence that expression of the B chain in cell types possessing PDGF receptors can drive such cells along the pathway to malignancy. The A chain is less potent than the B chain in inducing neoplastic transformation of cultured mouse (NIH/3T3) cells.

Recent studies have suggested the existence of two subtypes of the PDGF receptor (PDGF-R), on the basis of PDGF isoform binding and competition using mouse or human fibroblasts (27). These works are consistent with the hypothesis that there exists one receptor subtype which preferentially binds the B chain dimer, and another which efficiently binds all isoforms of the PDGF molecule. However, the results of these studies could not discriminate between two distinct possibilities with differing implications for the study and ultimate treatment of diseases involving such receptors: either these subtypes represent differently processed products of a single PDGF-R gene; or they are products of distinct genes.

Further, there have been conflicting findings concerning binding of different PDGF isoforms of the receptor produced by a previously identified human PDGF-R gene. Introduction of PDGF-R genes by expression vectors into different cell types devoid of PDGF receptors has been reported to lead either to preferential binding of PDGF-BB (14) or, alternatively, to efficient binding by all three isoforms (28). The basis of this discrepancy is not known.

Thus, there has been uncertainty concerning the ability of the known PDGF receptor to respond to different PDGF isoforms, and to the main AB heterodimer form of human PDGF, in particular. Some reported differences might be explained by cell specific differences in post-translational processing of the product of the known PDGF-R gene, or by the presence of accessory proteins in certain cell types. Alternatively, the different binding properties reported in different studies might be explained by the existence of two distinct genes encoding different PDGF receptors.

In light of the complexities of PDGF ligand and receptor activities described above, and the related processes which are influenced thereby, comprising both normal wound healing and abnormal connective tissue conditions, including neoplastic growth, arteriosclerosis, arthritis, and fibrotic diseases, it is apparent that there has been a need for methods and compositions and bioassays which would provide an improved knowledge and analysis of mechanisms of connective tissue growth regulation, and, ultimately, a need for novel diagnostics and therapies based on the PDGF receptors involved therein.

In particular, the observations above, indicate a specific need for thorough characterization of the genetic basis of PDGF receptor production. Furthermore, it has been shown previously (5) that it is possible to identify and clone novel related members of the gene family encoding membrane-spanning growth factor receptors with tyrosine kinase activity, which comprises the known PDGF receptor gene and the kit and fms oncogenes, by exploiting the conserved tyrosine kinase coding region as a probe.

Accordingly, the present invention contemplates the application of methods of recombinant DNA technology to fulfill the above needs and to develop means for producing PDGF receptor proteins which appear to be the predominant effectors of the main form of human PDGF. This invention also contemplates the application of the molecular mechanisms of these receptors related to healing and pathological processes.

In particular, it is an object of the present invention to identify and isolate the coding sequence of a novel human gene related to but distinct from the known PDGF-R gene, as well as from other members of the family of tyrosine kinase genes comprising the PDGF-R, kit, and fms genes. Further, it is an object of this invention to develop the molecular tools needed to establish the relative roles of the novel and known forms of PDGF receptor in physiological processes involving PDGF.

SUMMARY OF THE INVENTION

The present invention relates to a development of recombinant DNA technology, which includes production of novel PDGF receptor (PDGF-R) proteins, free of other peptide factors. Novel DNA segments, RNAs, and bioassay methods are also included.

The present invention in particular relates, in part, to DNA segments which encode messenger RNAs (mRNAs) and proteins having structural and/or functional characteristics of a new human receptor within the subfamily of membrane-spanning tyrosine kinase receptor genes comprising the following known receptor genes: the PDGF-R gene; colony stimulating factor one receptor (CSF1-R) gene (also known as a cellular form of the fms oncogene, c-fms); and a cellular form of the kit oncogene (c-kit) (see references 3, 6, and 7 for background).

More specifically, this invention includes DNA segments containing a genomic DNA sequence or a DNA sequence complementary to the mRNA transcribed from said genomic DNA (i.e., a "cDNA"), with a predicted protein product similar in structure to other receptors of this growth factor receptor subfamily. Among these receptors, the predicted novel gene product exhibits closest sequence homology to the known PDGF receptor.

Further, this novel product encoded by DNAs of this invention is coexpressed with the known PDGF receptor gene product in a variety of normal cell types. This protein product can bind to and be functionally activated by PDGF. However, the activities of different PDGF isoforms functionally distinguish the new product, herein designated the type α human PDGF receptor, from that of previously identified genes encoding receptors that can bind PDGF, including the known receptor previously call the PDGF receptor and herein designated as the type β PDGF receptor. Moreover, considerable evidence disclose herein indicates that this novel gene product, the type α PDGF receptor, is the main effector of activity for the most abundant form of PDGF in the human body.

In the practice of one embodiment of this invention, the DNA segments are capable of being expressed in suitable host cells, thereby producing the novel PDGF receptor proteins. This invention also relates to mRNAs produced as the result of transcription of the sense strands of the DNA segments of this invention. The invention further comprises novel bioassay methods for determining levels of expression in human cells of the mRNAs and proteins produced from the genes related to DNA segments of the invention.

In a principal embodiment, the present invention comprises DNA segments encoding novel PDGF receptors, as exemplified by the following: a clone of genomic normal human thymus DNA, herein designated as the T11 genomic clone; human cDNA clones of cell mRNAs containing sequences contained in T11, designated HF1, HB6, EF17 and TR4; and related DNA segments which can be detected by hybridization to any of the above human DNA segments, which related segments encode receptor genes, wherein said genes do not include previously known PDGF-related receptor genes.

The human gene related to clone T11 are referred to hereinafter as "the T11 gene" and use of the term "T11" as an adjective is intended to include any of the above DNA segments of this invention, absent a specific reference to "the T11 genomic clone".

In another embodiment, this invention relates to a recombinant DNA molecule comprising a vector and a DNA of the present invention. These recombinant molecules are exemplified by molecules comprising genomic or cDNA clones related to the T11 gene and any of the following vector DNAs: a bacteriophage λ cloning vector; or an expression vector capable of expressing inserted DNAs in mammalian cells.

In still another embodiment, the invention comprises a cell, preferably a mammalian cell, transformed with a DNA of the invention. Further, the invention comprises cells, including yeast cells and bacterial cells such as those of $E.$ $coli$ and $B.$ $subilis,$ transformed with DNAs of the invention. According to another embodiment of the invention, the transforming DNA is capable of being expressed in the cell, thereby increasing the amount of PDGF-R protein encoded by this DNA, in the cell.

Still further, the invention comprises novel PDGF-R proteins made by expression of a DNA of the invention, or by translation of an RNA of the invention. These receptors can be used for functional studies, and can be purified for additional biochemical and functional analyses, such as qualitative and quantitative receptor binding assays.

In particular, these type α PDGF receptors may be used for the development of therapies for conditions involving abnormal processes involving PDGF and its receptors, by testing receptor binding and activation activities of potential analogs (either (antagonists or agonists) of the various PDGF isoforms, including the main form of human PDGF.

According to this aspect of the invention, the novel PDGF-R proteins can be protein products of "unmodified" DNAs and mRNAs of the invention, or they can be modified or genetically engineered protein products. As a result of engineered mutations in the DNA sequences, modified PDGF-R proteins have one or more differences in amino acid sequence from the corresponding naturally occurring "wild-type" proteins. These differences may impart functional differences to the modified gene products such as improvements in their manufacturability or suitability for use in bioassays.

This invention also relates to novel bioassay methods for detecting the expression of genes related to DNAs of the invention. According to one such embodiment, DNAs of this invention, particularly the most preferred DNAs, may be used as probes to determine specific levels of mRNAs related to type α PDGF receptors, without interference from mRNAs of known PDGF receptor genes. Such bioassays may be useful, for example, for identification of various classes of tumor cells or of genetic defects in connective tissue growth and/or the healing response.

This invention further comprises novel antibodies made against a peptide encoded by a DNA segment of the invention or by a related DNA. In this embodiment of the invention, the antibodies are monoclonal or polyclonal in origin, and are generated using PDGF receptor-related polypeptides from natural, recombinant or synthetic chemistry sources. These antibodies specifically bind to a PDGF-R protein which includes the sequence of such polypeptide. Preferably, these antibodies bind only to type α PDGF receptor proteins or, alternatively, only to type β PDGF receptor proteins. Also, preferred antibodies of this invention bind to a PDGF receptor protein when that protein is in its native (biologically active) conformation.

Fragments of antibodies of this invention, such as Fab or F(ab)' fragments, which retain antigen binding activity and can be prepared by methods well known in the art, also fall within the scope of the present invention. Further, this invention comprises pharmaceutical compositions of the antibodies of this invention, or active fragments thereof, which can be prepared using materials and methods for preparing pharmaceutical compositions for administration of polypeptides that are well known in the art and can be adapted readily for administration of the present antibodies without undue experimentation.

These antibodies, and active fragments thereof, can be used, for example, for specific detection or purification of either the novel type α PDGF receptor, or, alternatively, of the known type β PDGF receptor. Such antibodies could also be used in various methods known in the art for targeting drugs to tissues with high levels of PDGF receptors, for example, in the treatment of appropriate tumors with conjugates of such antibodies and cell killing agents.

BRIEF DESCRIPTION OF THE FIGURES

Specifically, FIG. 1A shows hybridization of a v-fms probe to human placenta (lane 1 and 3) or thymus (lane 2 and 4) DNAs under stringent (50% formamide; lane 1 and 2) or relaxed (30% formamide; lane 3 and 4) hybridization conditions.

FIG. 1B shows hybridization of a mouse PDGF receptor probe to human placenta (lane 1 and 3) or thymus (lane 2 and 4) DNAs under stringent (50% formamide; lane 1 and 2) or relaxed (30% formamide; lane 3 and 4) hybridization conditions. Arrows indicate the 12-kbp EcoRI fragment detected under relaxed conditions by both v-fms and mouse PDGF-R probes.

FIG. 2 presents the restriction map of the novel v-fms-related gene (T11) and related human PDGF receptor cDNA clones.

Specifically FIG. 2 shows a schematic drawing of the molecular cloning of the λT11 genomic fragment as well as cDNAs of T11 and PDGF-R cDNA genes. Restriction map of T11 cDNA is shown in solid bars; and PDGF-R cDNA is shown in open bars. Coding regions withing three fragments, as determined by nucleotide sequencing analysis, are indicated by black boxes labeled, l, b and c.

FIG. 3 contains the nucleotide sequence and deduced amino acid sequence of the novel type α PDGF receptor encoded by the T11 gene.

Specifically, the nucleotides are numbered at the left. The predicted amino acid sequence of the long open reading frame is shown above the nucleotide sequence. Amino acids are numbered over the amino acids, starting at the putative initiation codon. The potential N-terminal signal sequence is underlined. Potential sites of N-linked glycosylation are overlined, and cysteine residues are boxed. The putative single transmembrane region is indicated by a shaded bar. The potential ATP binding site in the kinase domain is indicated by circles over Gly at residues 600, 602 and 605 and Lys at residue 627. The putative tyrosine autophosphorylation site at residue 849 is indicated by *. The regions of the λT11 genomic sequence defined by exons a, b and c are underlined. The AATAAA box close to the polyadenylated 3' end of the cDNA is underlined as well.

FIG. 4A depicts results of hydrophobicity analysis of human type α PDGF receptor and and FIG. 4B depicts homologies of deduced amino acid sequences in comparison with the known type β PDGF receptor and other receptors.

The schematic diagram in FIG. 4B of the predicted protein domains shows the signal sequence (S; black box), ligand binding domain (LB), transmembrane domain (TM; second black box), juxtamembrane domain (JM), tyrosine kinase domains (TK1, TK2; hatched boxes), interkinase domain (IK) and carboxyl terminus (C). The hydropathicity profile was calculated by the method of Kyte and Doolittle, J. Mol. Biol., 157:105 (1982).

Figure 5A:
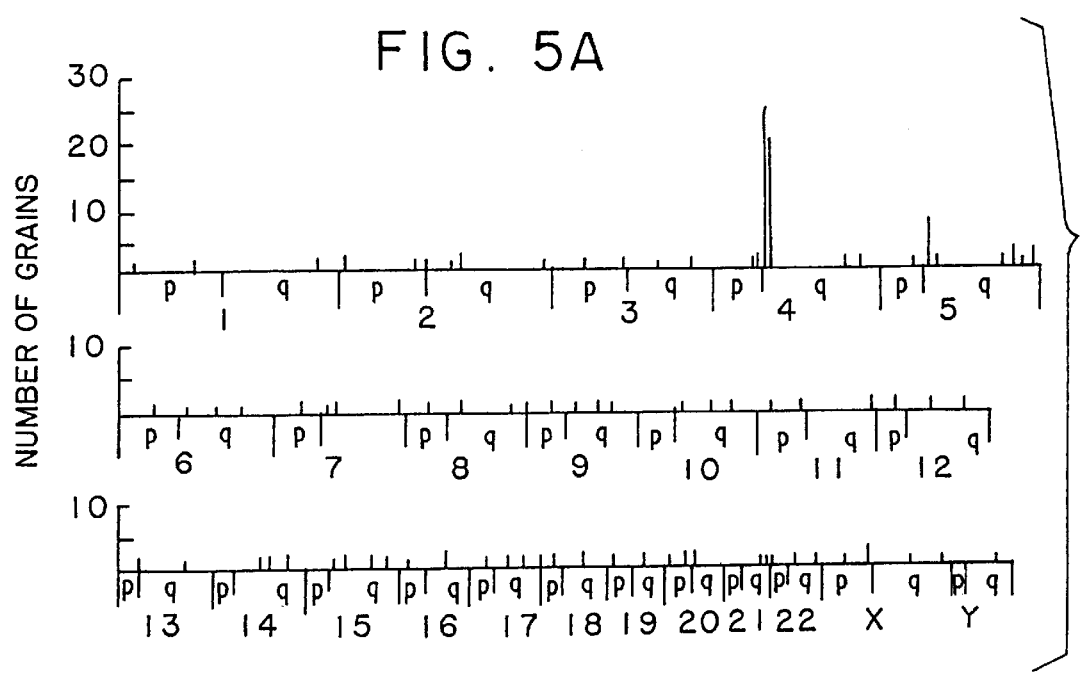
Figure 5B:
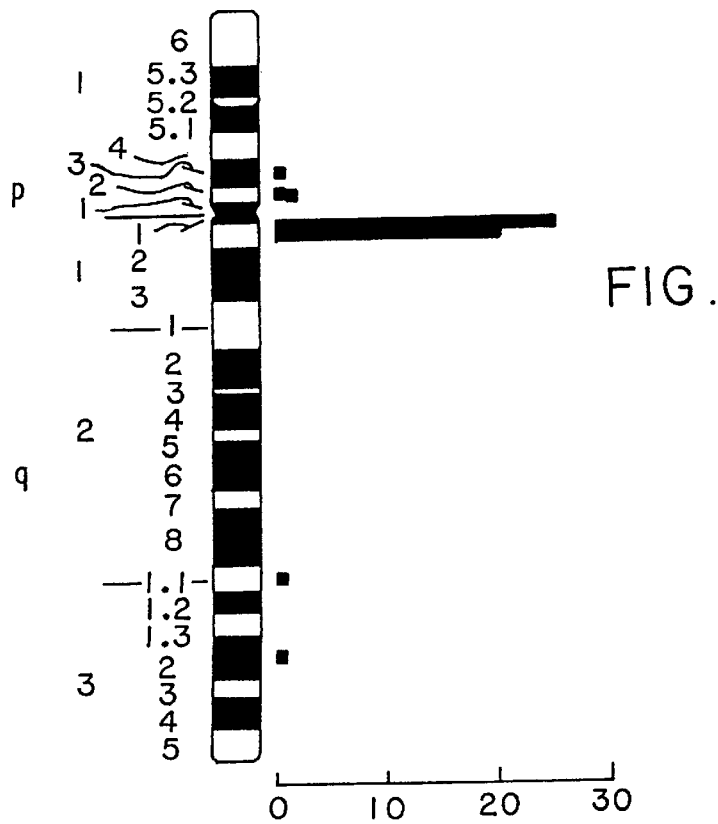

FIG. 5A and FIG. 5B show chromosome mapping of the type α PDGF receptor gene.

FIG. 5A shows the distribution of silver grains on normal human chromosomes by in situ hybridization with pT11-P probe (clone of the 3.6-kbp PstI genomic fragment), as shown in FIG. 2. FIG. 5B shows the distribution of grains on chromosome 4.

FIGS. 6A–6D show a comparison of mRNA species produced from the type α and β PDGF receptor genes.

Figure 6A:
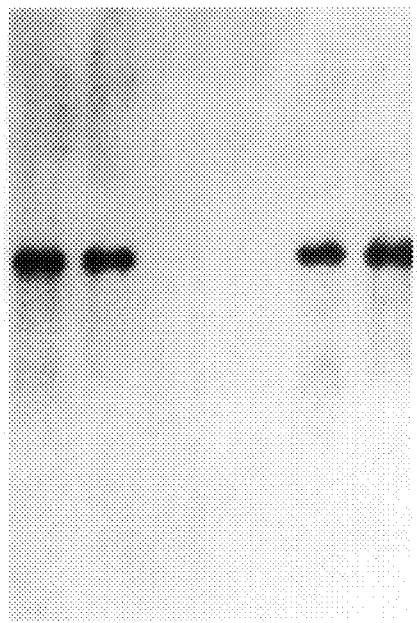
Figure 6B:
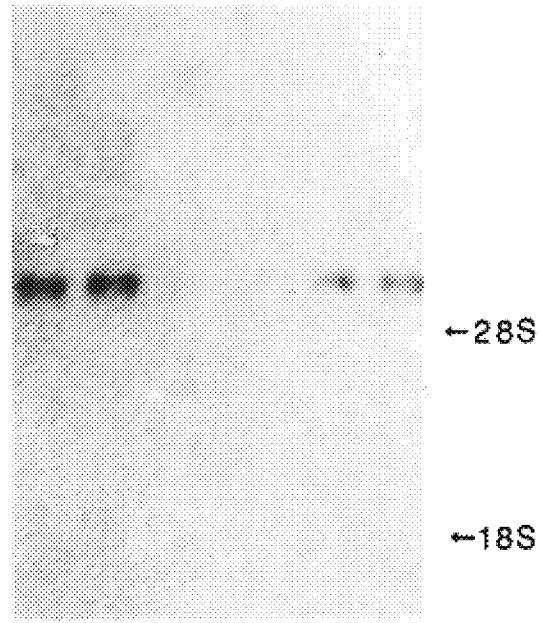
Figure 6C:
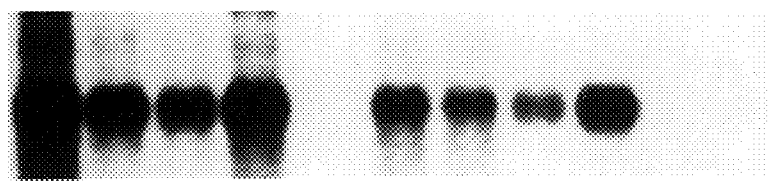
Figure 6D:
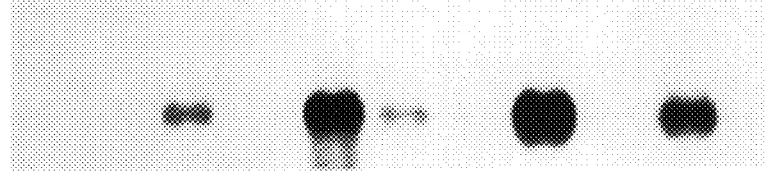

The same filter was first hybridized with the probe from pT11-HP (0.95-kbp HindIII-PstI genomic fragment) (FIG. 6A) and then rehybridized with a PDGF-R cDNA probe (FIG. 6B). A different filter was first hybridized with T11 cDNA (3.5-kbp Bam HI fragment of TR4 including the whole coding region) (FIG. 6C) and then rehybridized with PDGF-R cDNA (3.8-kbp NdeI fragment of HPR2) (FIG. 6D). FIGS. 6A and 6B contained poly (A)+RNAs (5 μg per lane) extracted from human smooth muscle (lane 1), heart (lane 2), liver (lane 3), spleen (lane 4) or embryo (lanes 5 and 6) . FIGS. 6C and 6D contained total RNA (20 μg per lane) extracted from G402 leiomyoblastoma cells (lane 1), SK-LMS-1 leiomyosarcoma cells (lane 2), A1186 or A204 rhabdomyosarcoma cells (lanes 3 and 4), 8387 fibrosarcoma cells (lane 5), astrocytoma tissues (lanes 6 and 7), A1690 astrocytoma cells (lane 8), A1207 or A172 glioblastoma cells (lanes 9 and 10) or A875 melanoma cells (lane 11). Migrations of 28S and 18S ribosomal RNA (markers) are as indicated.

Figure 7A:
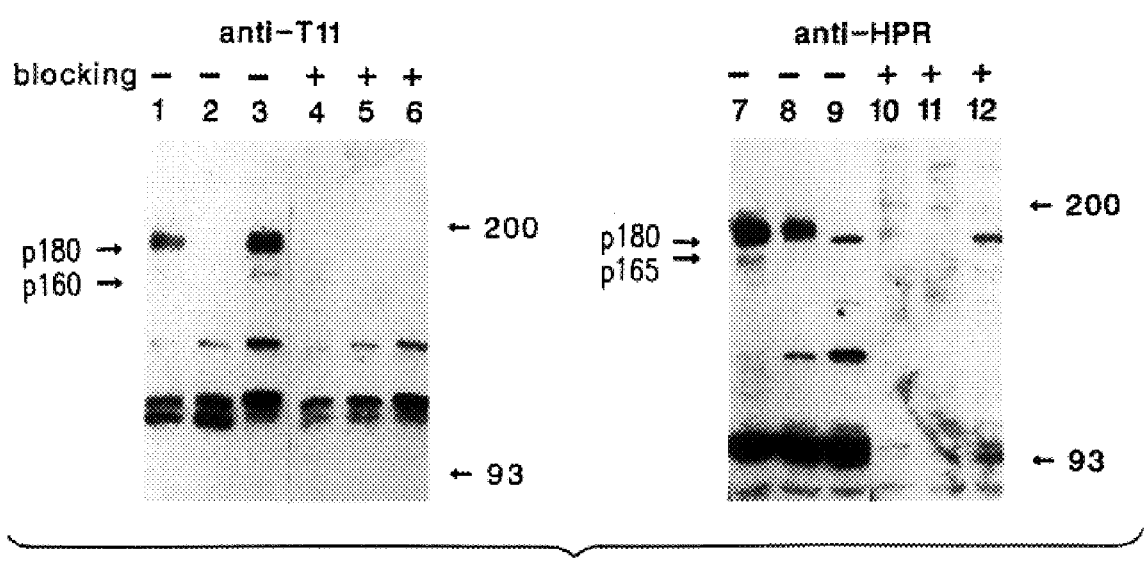
Figure 7B:
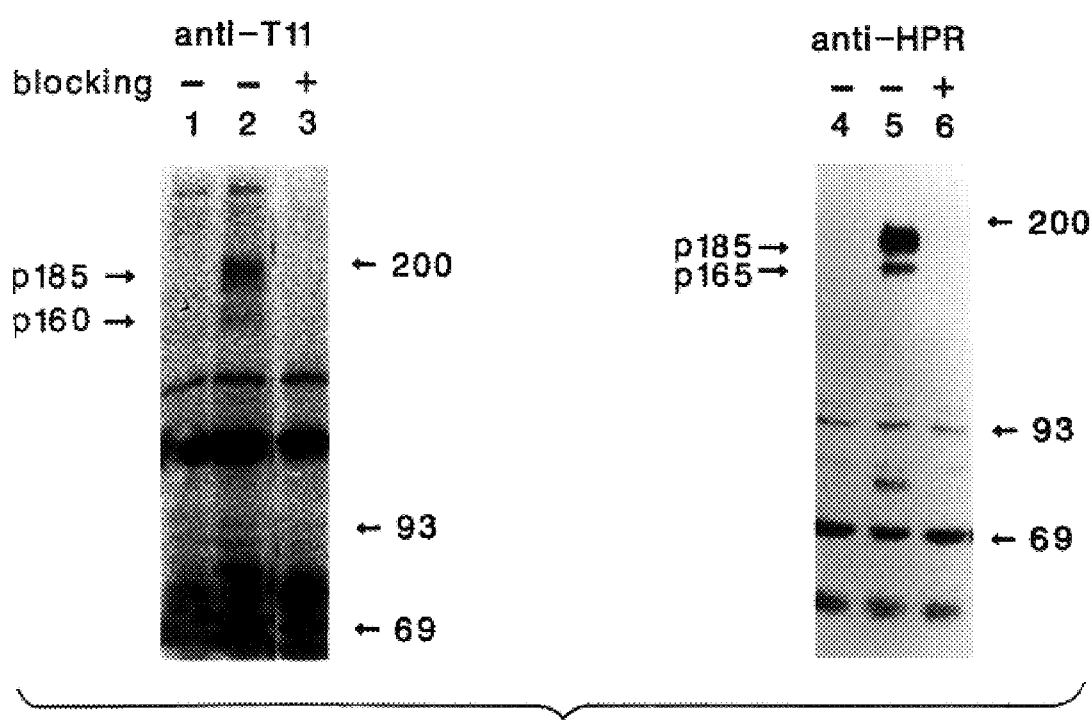

FIGS. 7A and 7B demonstrate specific detection of type α or type β proteins with peptide antisera in human cell lines or in monkey (COS-1) cells transformed with a T11 DNA in an expression vector.

FIG. 7A shows the detection of T11 and PDGF-R proteins with peptide antisera in human cells lines. M426 human embryo fibroblasts are shown in lanes 1, 4, 7 and 10, 8387 fibrosarcoma cells in lanes 2, 5, 8 and 11, A204 rhabdomyosarcoma cells in lanes 3, 6, 9 and 12. FIG. 7B shows the detection of T11 and PDGF-R proteins with peptide antisera in COS-1 cell transfectants. COS-1 cells are shown in lanes 1 and 4, COS-1 cells transfected with vectors carrying T11 cDNA are shown in lanes 2 and 3 and PDGF-R cDNA are shown in lanes 5 and 6.

Figure 8:
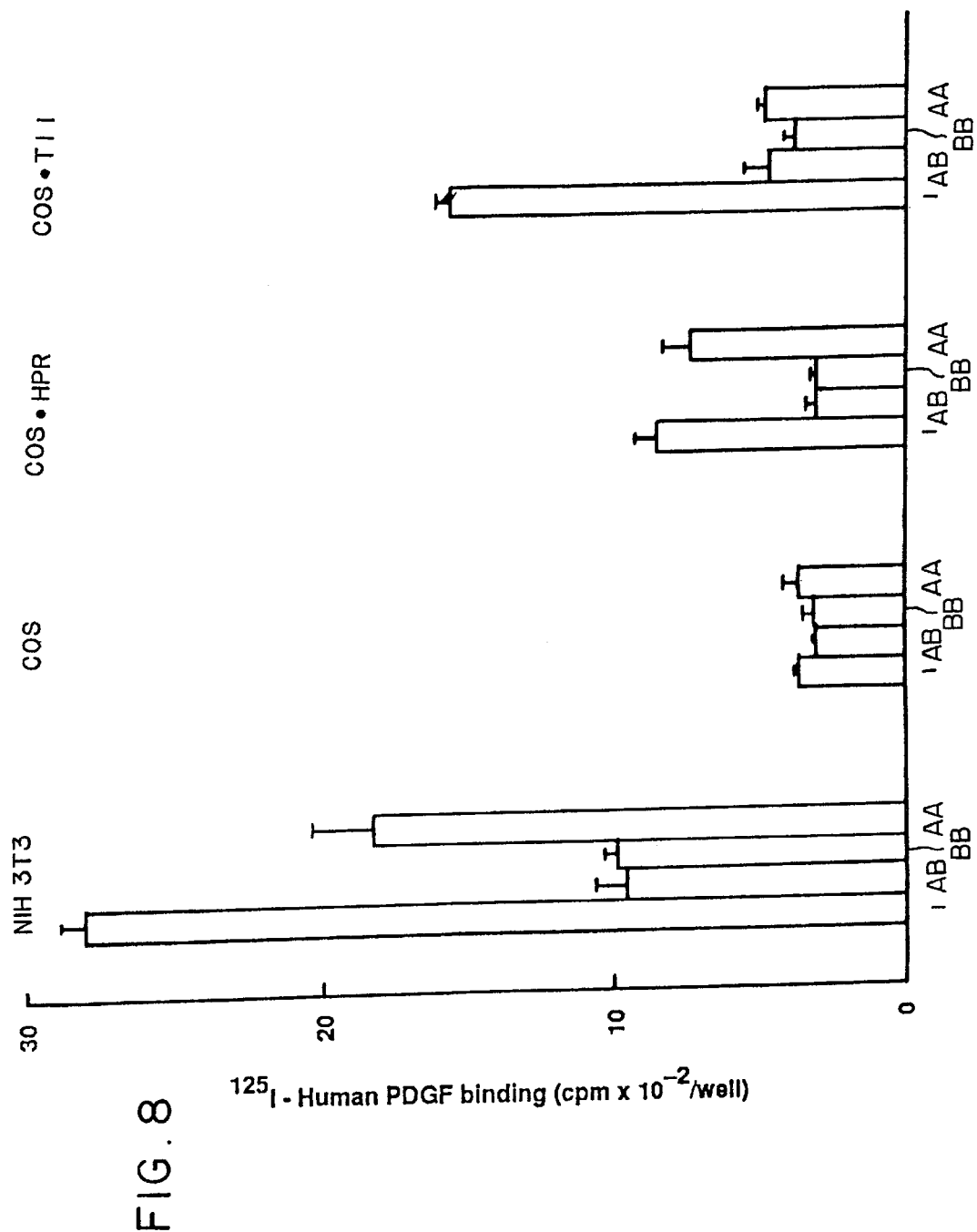

FIG. 8 displays binding of ($^{125}$I-labeled) human PDGF to mouse cells (NIH/3T3), control COS-1 cells and COS-1 cells transformed with T11 or known PDGF-R cDNA expression vectors. Results represent the mean values (±SD) of triplicate samples FIGS. 9A–9C demonstrate tyrosine autophosphorylation of type α and type β PDGF receptors in response to various isoforms of PDGF.

Figure 9A:
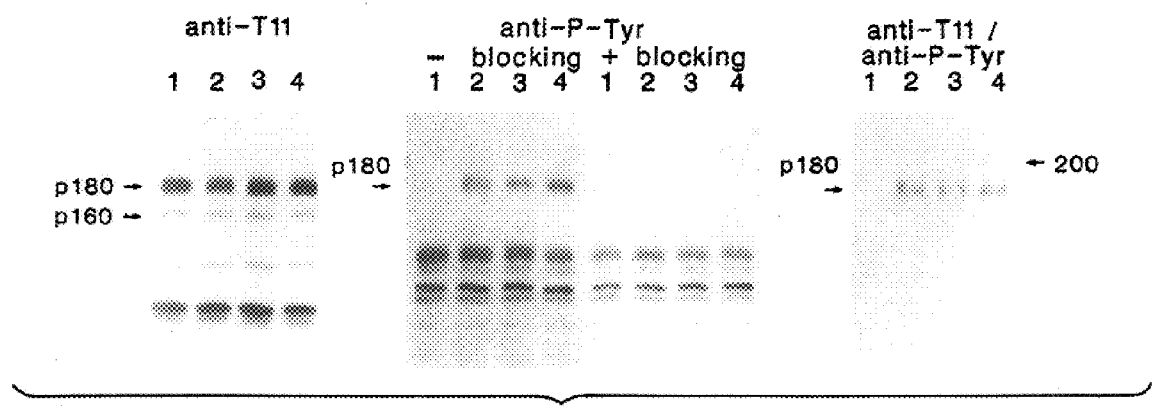
Figure 9B:
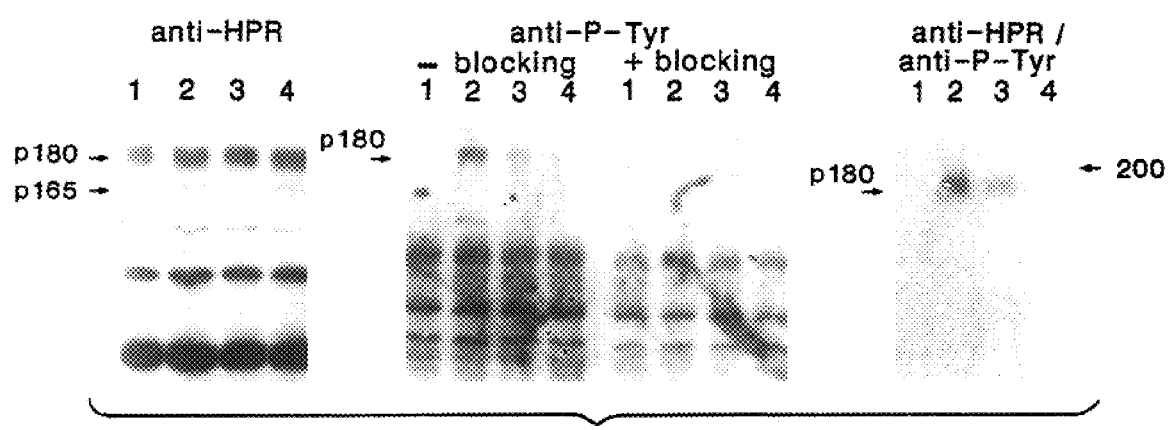
Figure 9C:
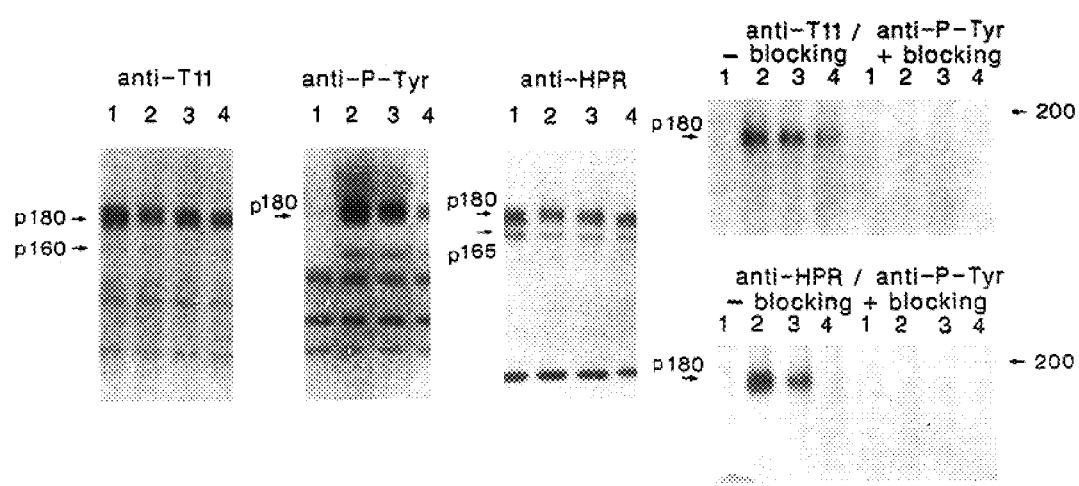
Figure 10B:
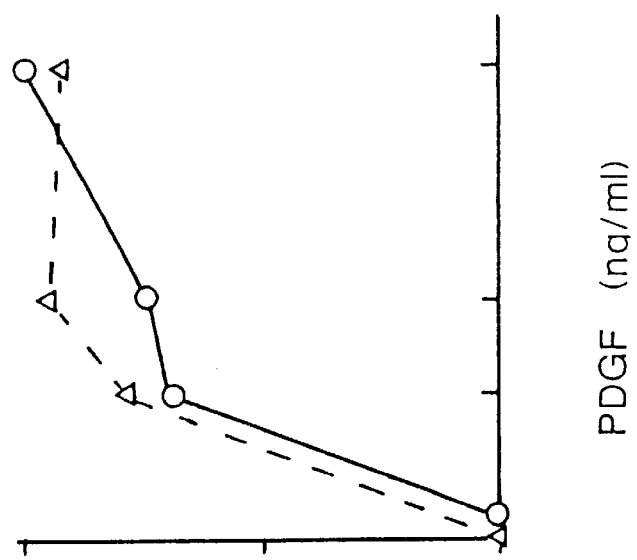
Figure 10A:
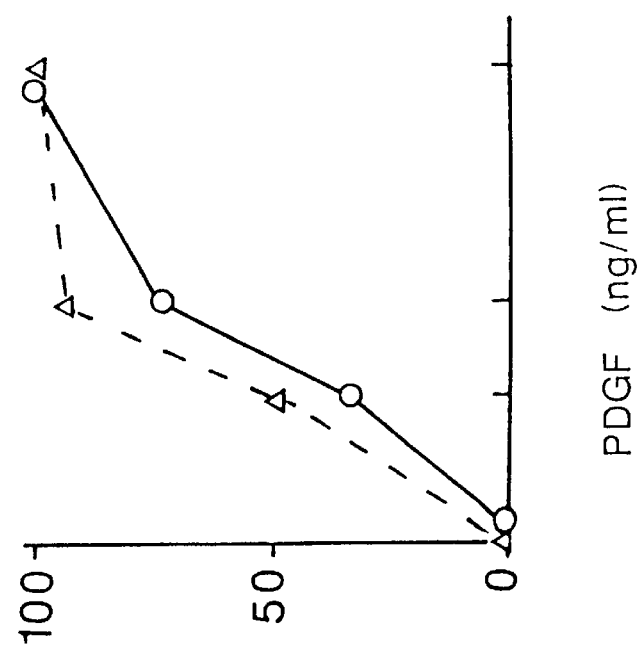
Figure 10D:
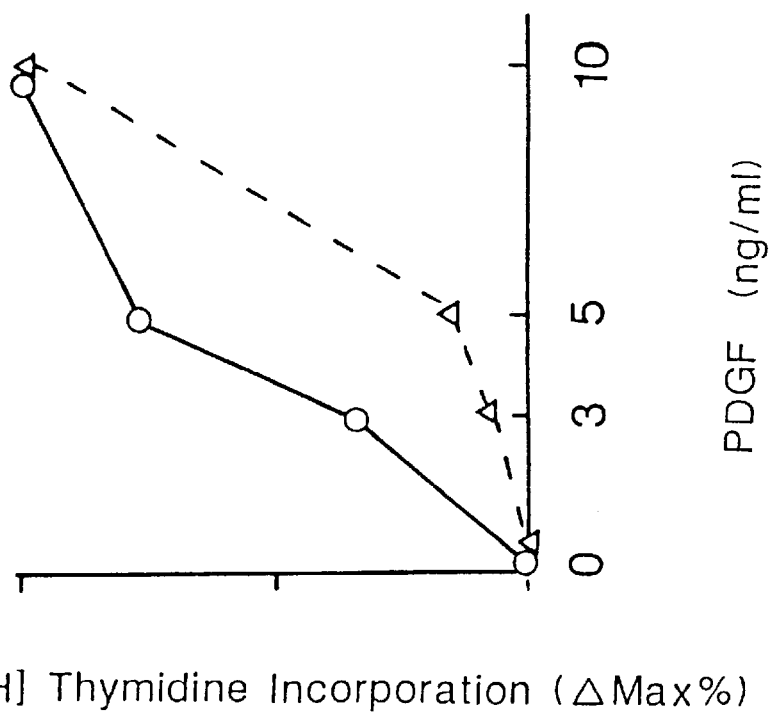
Figure 10C:
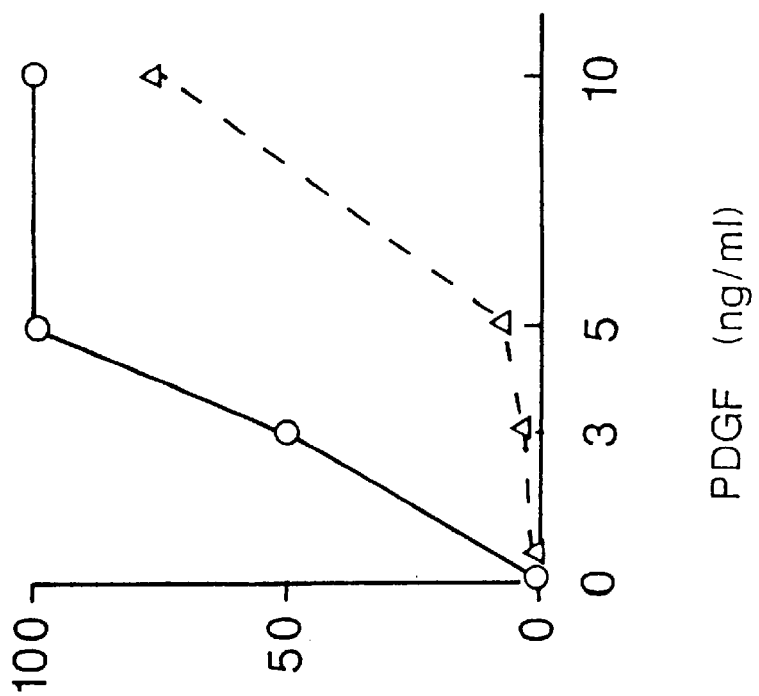

FIG. 9A shows A204 cells, FIG. 9B shows 8387 cells and FIG. 9C shows NIH/3T3 cells, incubated with PDGF-BB (30 ng/ml) (lane 2), human PDGF (30 ng/ml) (lane 3), PDGF-AA (300 ng/ml) lane 4 or 3 mM acetic acid (vehicle control: lane 1). Cell lysates were immunoprecipitated with peptide antisera directed against predicted type α or type β PDGF receptors (anti-T11 and anti-HPR, respectively). Immunoblot analyses were with antibodies to the receptors or phosphotyrosine (anti-P-Tyr) as indicated above the blots. Arrows indicate the specific bands which were blocked in the presence of immunizing peptide.

FIGS. 10A–10D show preferential stimulation of DNA synthesis by PDGF isoform AB (triangles) or PDGF isoform BB (circles) in various cells, as follows: mouse NIH 3T3 (FIG. 10A); human M426 (FIG. 10B); human AG1523 (FIG. 10C); and human M413 (FIG. 10D), with higher levels of type α PDGF receptor than type β receptor.

Figure 11:
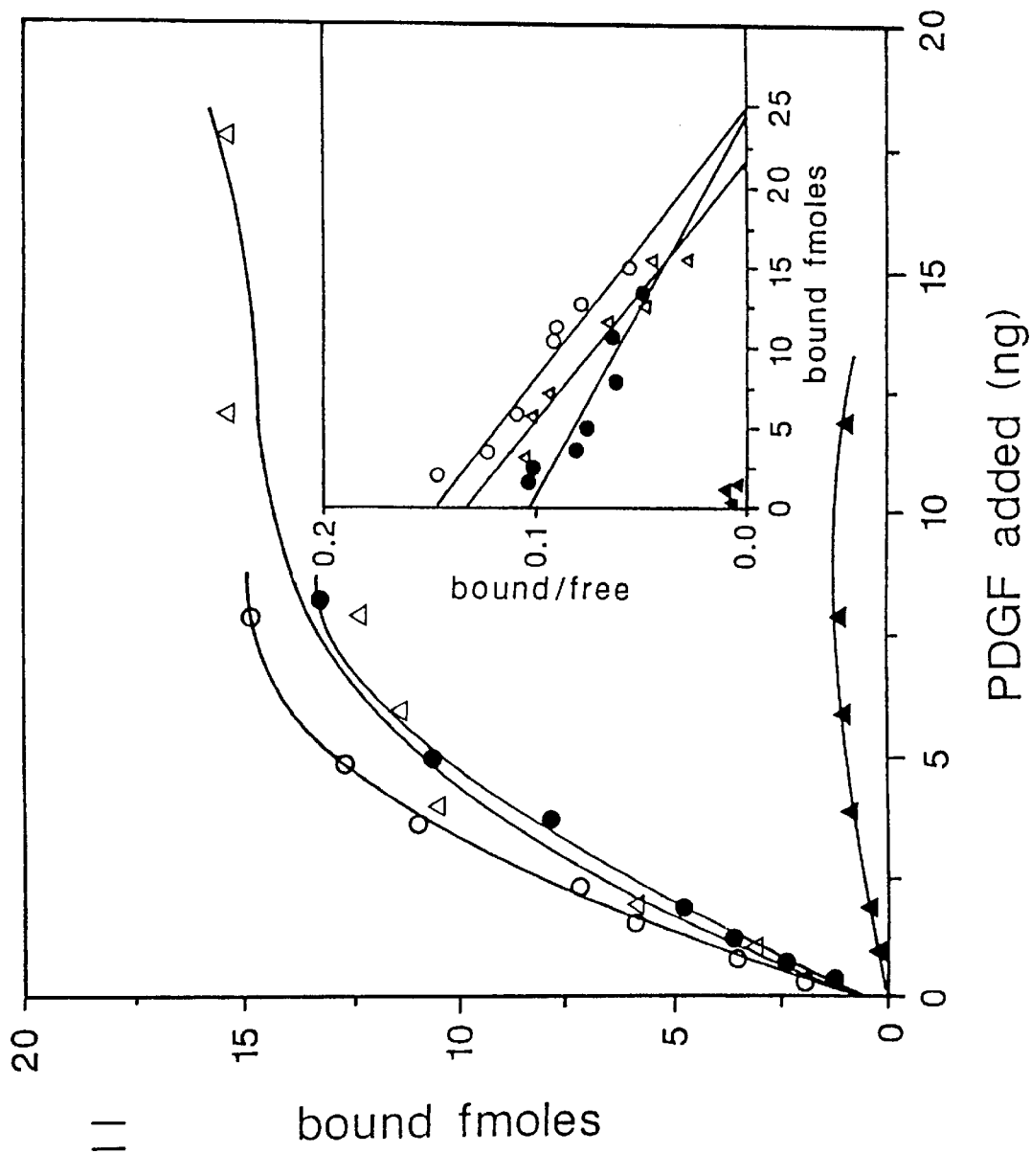

FIG. 11 presents binding data for type α (open symbols) and type β (filled symbols) PDGF receptors on (human 32D) cells transfected with vectors bearing the respective cDNAs, demonstrating that the type β receptor shows a strikingly lower affinity for the PDGF-AB form. The inset displays the same data replotted in the standard (semi-log) Scatchard format.

Figure 12A:
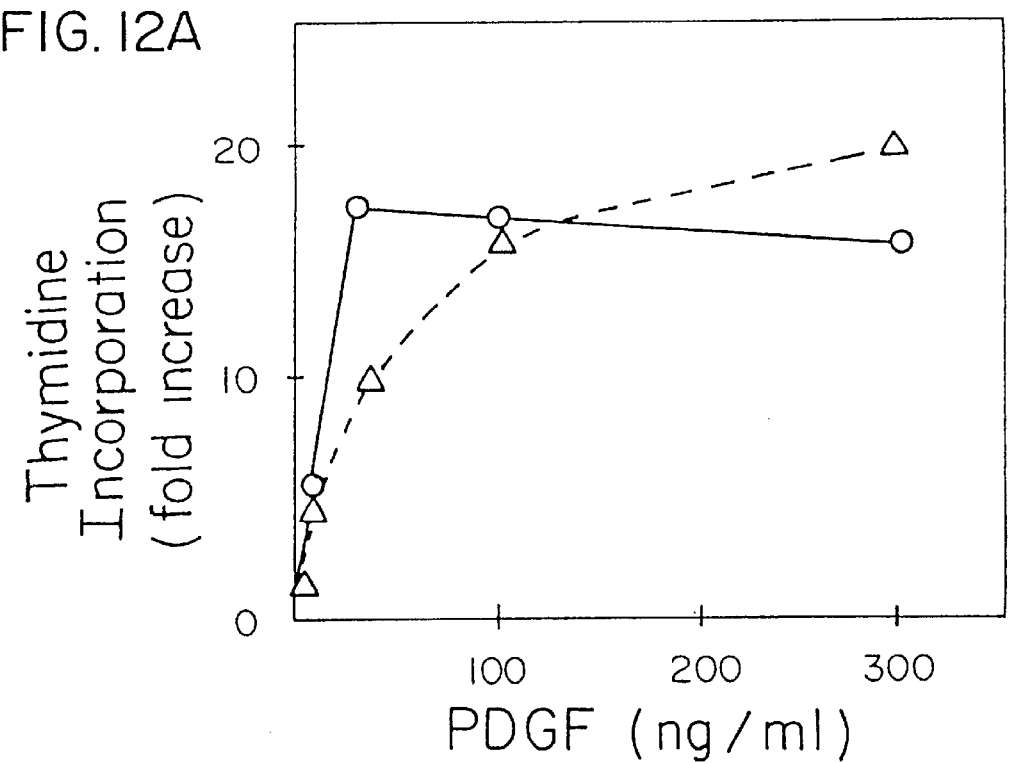
Figure 12B:
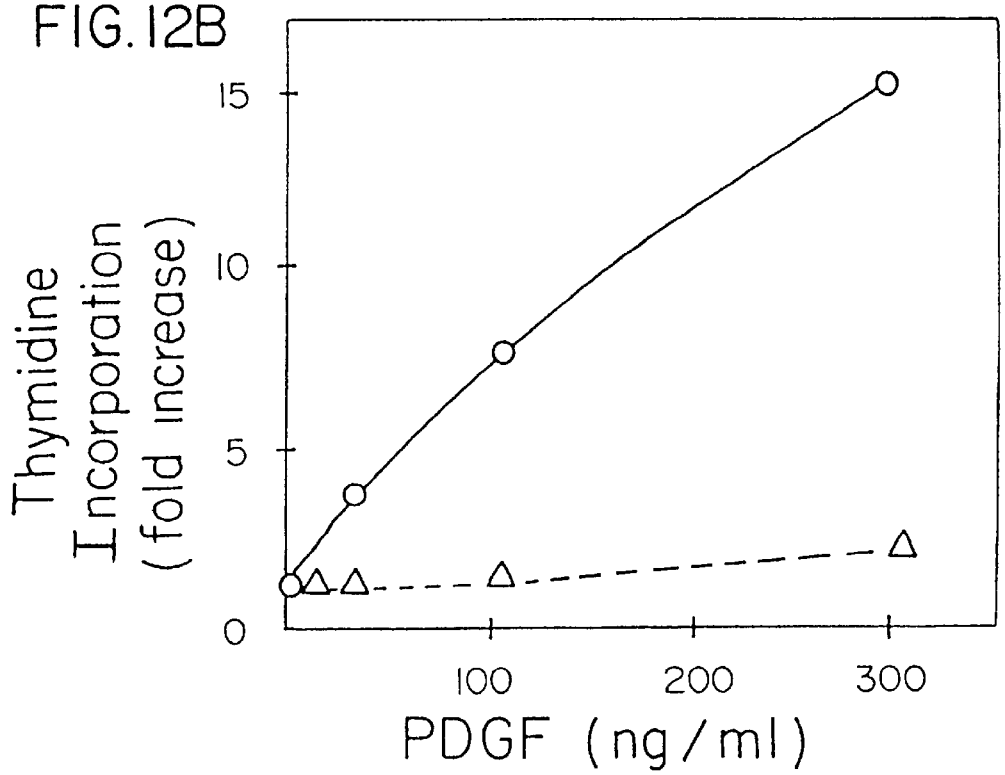

FIG. 12A and 12B illustrate the similar mitogenic responses to PDGF-BB (circles) by cells containing either type α (FIG. 12A) or type β (FIG. 12B) PDGF-R and the significantly lesser DNA synthesis response to PDGF-AB (triangles) in the type β, compared to type α receptor containing cells.

Figure 13A:
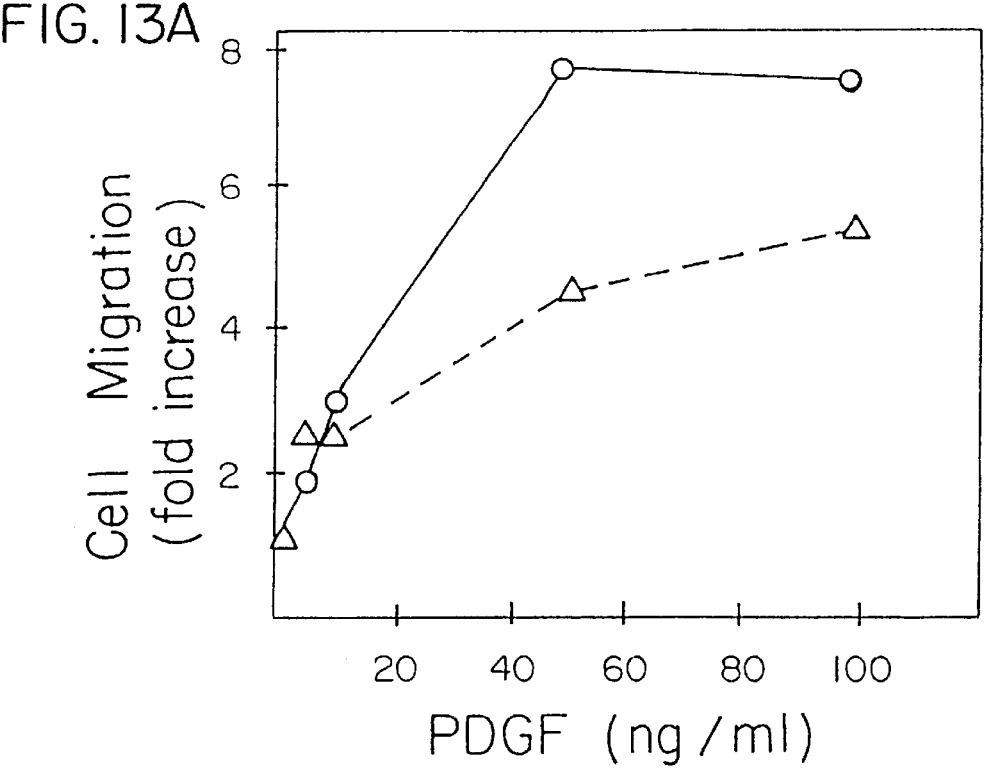
Figure 13B:
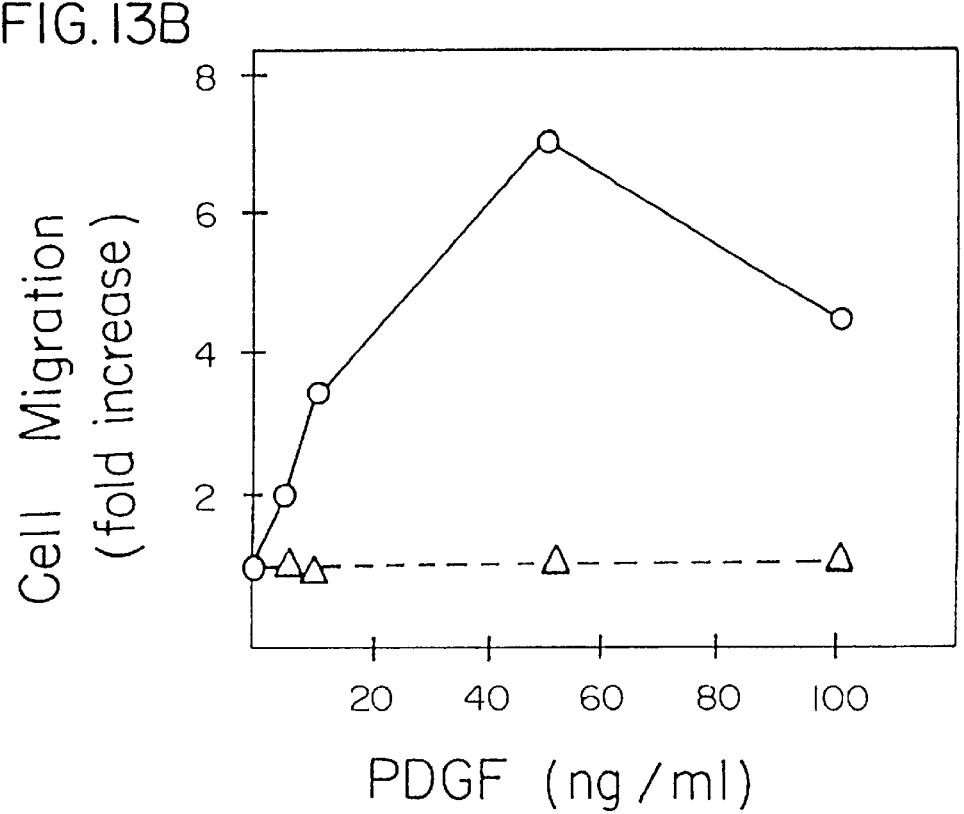

FIG. 13A and 13B demonstrate equivalent chemotaxic cellular responses to PDGF-BB (circles) in cells with type α (FIG. 13A) or β (FIG. 13B) PDGF-R, whereas PDGF-AB (triangles) elicited a considerably lower chemotaxic response with type β receptors than with type α receptors.

Figure 14A:
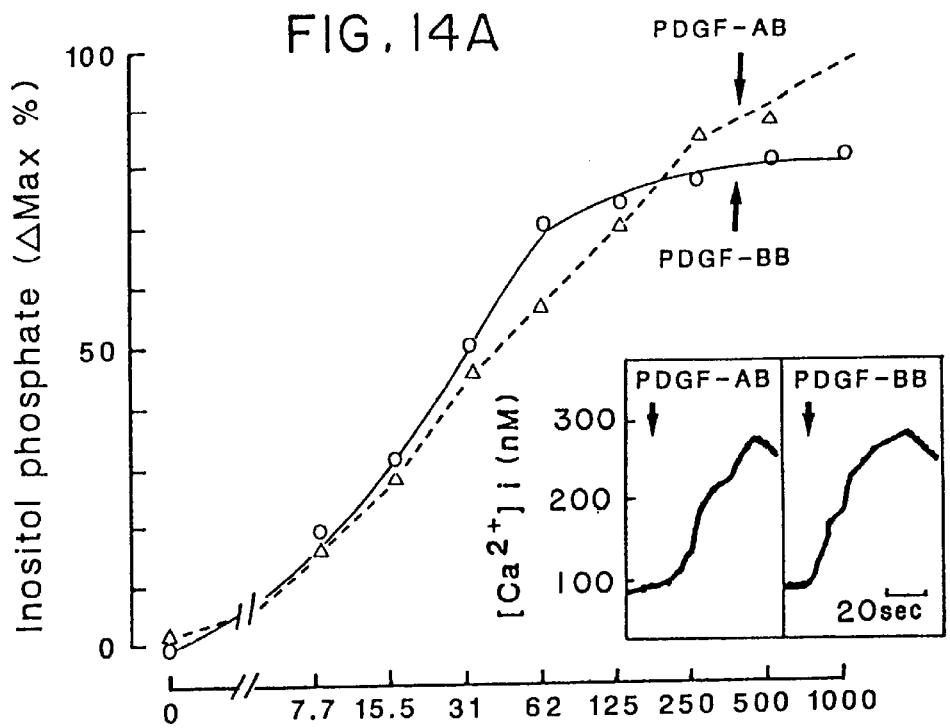
Figure 14B:
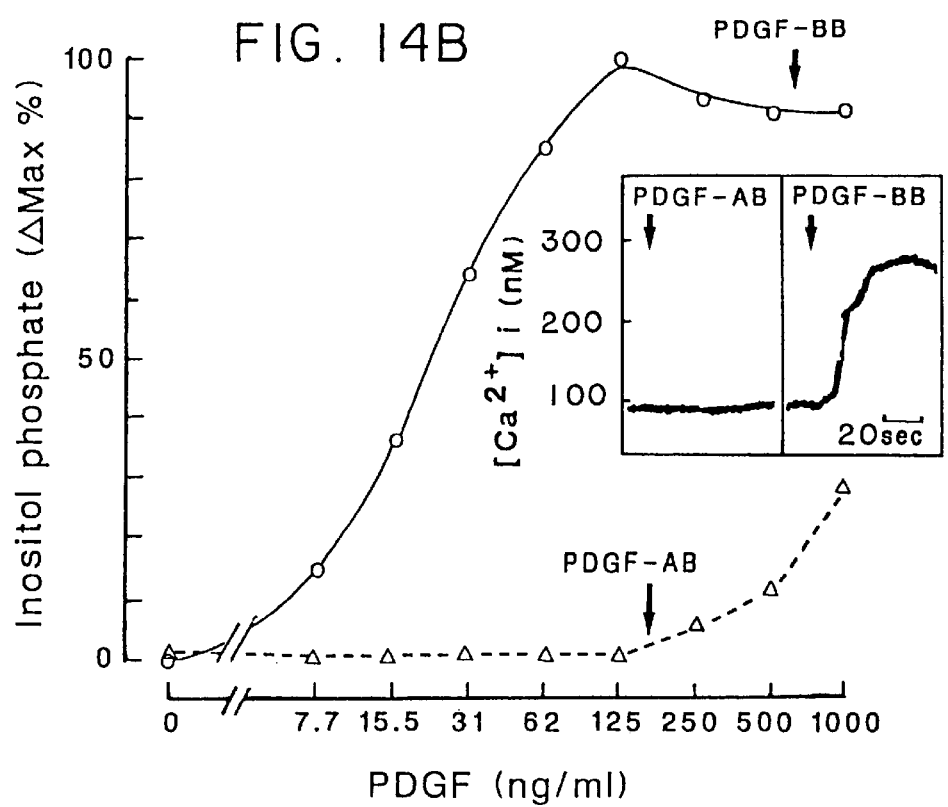

FIG. 14A and 14B show the effect of PDGF-AB (triangles) and PDGF-BB (circles) on inositol phosphate formation and cytosolic calcium mobilization ($[Ca^{2+}]i$) in cells bearing type α (FIG. 14A) and type β (FIG. 14B) PDGF-R, with the type α receptors again responding more efficiently to PDGF-AB.

DESCRIPTION OF SPECIFIC EMBODIMENTS

The DNAs of this invention are exemplified by DNAs referred to herein as: the T11 genomic clone; and clones HF1, HB6, EF17 and TR4, comprising human cDNA clones of cell mRNAs containing sequences included in the T11 genomic clone.

The T11 genomic clone and the TR4 cDNA clone are preferred DNAs of this invention. A clone designated pT11-HP (a HindIII-PstI 0.95-kbp fragment of genomic clone T11) and a particular restriction fragment from a T1 cDNA (3.5-kbp BamHI fragment of TR4, including the whole coding region) are most preferred DNAs of this invention.

The restriction enzyme digestion maps of cDNA clones HF1, HB6, EF17 and TR4, and their mapping relationships to genomic clone T11, are displayed in FIG. 2. The sense strand DNA nucleotide sequence, and the predicted primary protein sequence encoded, are shown in FIG. 3 for the TR4 cDNA clone, the largest cDNA clone related to the T11 gene.

Figure 1A:
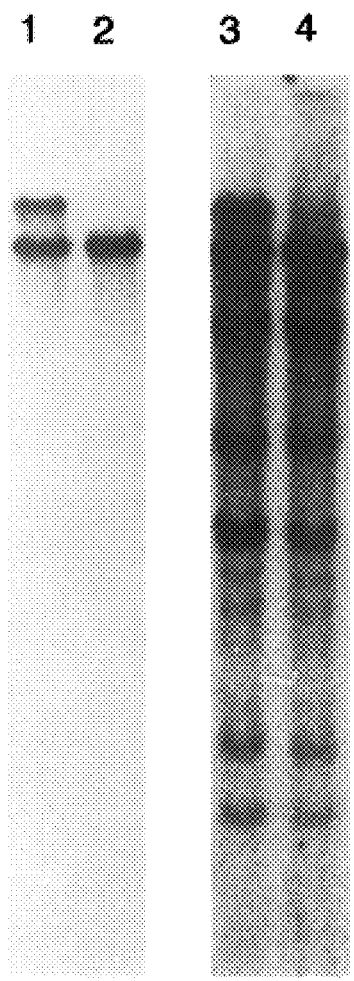
FIGS. 1A and 1B illustrate the detection of gene fragments related to the oncogene v-fms and to the known mouse PDGF receptor in human placenta and thymus DNAs by Southern blot hybridization analyses.
Figure 1B:
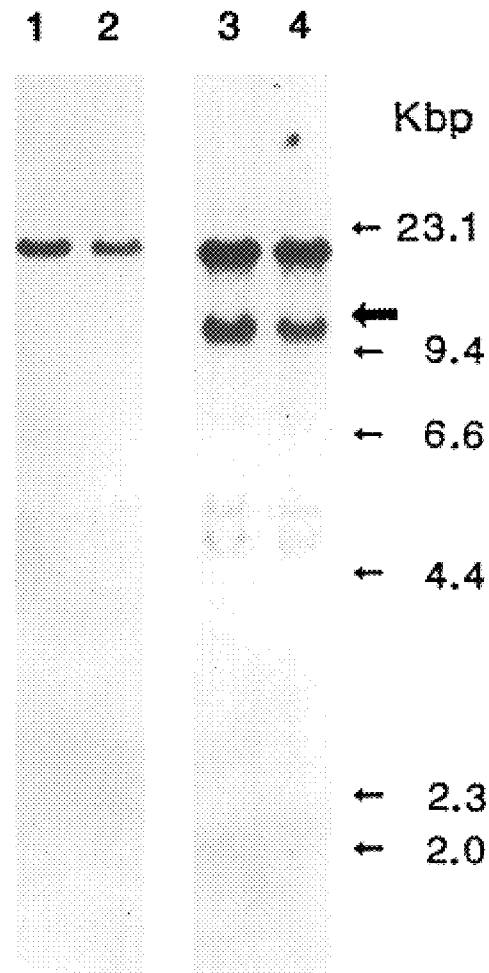

As described in the Experimental Section, the T11 genomic clone comprises a clone of genomic fragment of normal human thymus DNA containing a 12-kbp sequence bounded by recognition sites for the restriction enzyme EcoRI, which fragment hybridized more strongly in analyses by blot hybridization than other fragments with DNA probes derived from the tyrosine-kinase domains of both the viral oncogene v-fms and the mouse cellular PDGF-R gene (see FIG. 1). The T11 genomic clone contains most of the blocks of sequences found in the mRNA product of the T11 gene (i.e., the exons), in addition to intervening gene sequences not found in the mRNA (i.e., introns).

Other DNAs of this invention include the recombinant molecules comprising T11-related genomic or cDNA clones of this invention and any of the following vector DNAs: a bacteriophage λ cloning vector (exemplified by λEMBL4 or λgt11); or a mammalian expression vector (such as the pSV2 gpt vector into which the simian sarcoma virus promoter was engineered) capable of expressing inserted DNAs in mammalian (e.g., COS-1) cells.

Genomic clone T11 DNA was isolated, by standard gene cloning methods well known in the art, from a genomic library constructed from EcoRI-digested normal human thymus DNA which was size-selected by sucrose gradients and cloned into the λEMBL-4 vector system. The λT11 clone was identified on the basis of hybridization with both v-fms and mouse PDGF-R probes only under relaxed but not stringent hybridization conditions. Further details of the cloning strategy and probes are provided below and in the following Experimental Section.

A plasmid containing the HF1 cDNA clone, designated pHF1, was isolated by standard, well known methods, from a normal human fibroblast cDNA library in the Okayama-Berg expression vector under stringent conditions using the 0.9-kbp HindIII-PstI fragment of λT11 which is a most preferred DNA of this invention. It contains a 3.9-kbp cDNA insert which hybridized to a 6.4-kb RNA transcript in normal human fibroblasts and contains a polyadenylation signal followed by a poly(A) tail at its 3' end. It also contains the coding sequence within the λT11 DNA and 170 nucleotides related to CSF1-R and PDGF-R tyrosine kinase domains upstream of exon (a).

The cDNA clone λHB6 was isolated by standard methods using the 0.4-kbp 5' end of clone HF1 to screen a human infant brain cDNA library in the λgt11 vector.

Another cDNA clone, λEF17, isolated by screening a human embryo fibroblast (M426 cell line) cDNA library, prepared by random priming of DNA synthesis on mRNA template and cloning in the λgt11 vector, with a 0.2-kbp 5' fragment of λHB6 as a probe. A possible ATG initiation codon was identified within EF17.

The three overlapping clones (pHF1, λHB6 and λEF17) contain the entire coding region in addition to 138-bp 5' and ˜3-kbp of 3' untranslated sequences (FIG. 2).

Figure 4:
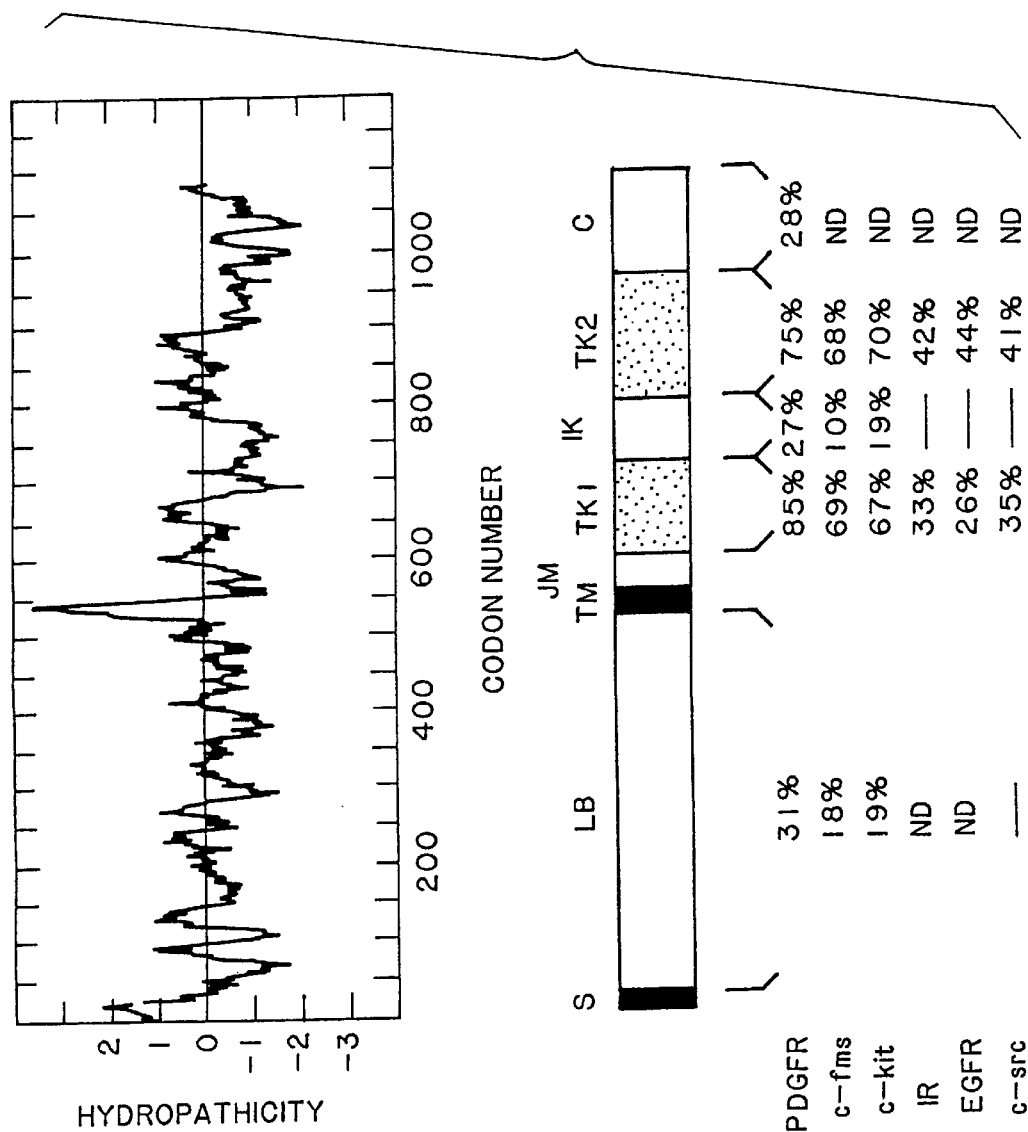

The cDNA clone TR4 was obtained using a 5' 0.2-kbp subfragment of λEF17 to screen a M426 human embryo fibroblast cDNA library in a "phagemid" (phage and plasmid hybrid) vector (10). The 6.4-kbp TR4 cDNA clone includes an open reading frame beginning with a possible ATG initiation codon at nucleotide position 139 and extended to a TAA termination codon at position 3406 (see FIG. 3). Moreover, the first 23 amino acid stretch displayed properties of a cleavable hydrophobic signal peptide (FIG. 3 & 4). The open reading frame was followed by ˜3-kbp of untranslated sequences and a polyadenylation signal (AATAAA) located 25 nucleotides upstream from the poly(A) sequence at the 3' end of the cDNA.

cDNA expression plasmids were constructed using standard cloning methods well known in the art, by introducing the T11-related cDNA encompassing nucleotides 1 to 3454 (FIG. 3) into the pSV2 gpt vector into which the simian sarcoma virus long-terminal-repeat (LTR) had been engineered as the promoter, as previously described in detail (49).

DNAs and sense strand RNAs of this invention can be employed, in conjunction with protein production methods known in the art, to produce cells expressing functional type α PDGF-R protein from the novel gene in the absence of other PDGF receptors. These novel receptors can be used for functional studies in cells, such as qualitative and quantitative receptor binding assays.

Accordingly, one embodiment of this aspect of this invention comprises a cell, preferably a mammalian cell, transformed with a DNA of the invention, wherein the transforming DNA is capable of being expressed. Mammalian cells (COS-1) transformed with the pSV2 gpt vector carrying a T11-related cDNA were prepared according to well-known methods and were shown to express T11 gene products as 185 kd and 160 kd species (FIG. 7B). These products were capable of binding human PDGF isolated from platelet, as illustrated in the Experimental Section below (see, FIG. 8).

Additional work in the Experimental Section demonstrates further that DNAs of this invention can be used to reconstitute type α PDGF receptor gene function in other cells free of PDGF receptors, and that each receptor type, α or β, efficiently mediates major known PDGF activities including mitogenic signal transduction, chemotaxis and stimulation of phosphoinositide turnover. Moreover, these studies further establish the type α PDGF receptor as the principal receptor for the main form of human PDGF which is derived from platelets.

Thus, by so using the DNAs of the invention in gene expression methods, especially the preferred TR4 cDNA clone listed herein, those skilled in the art, without undue experimentation, can construct cell systems which fall within the scope of this invention, for determining the mechanisms of PDGF regulatory processes, as well as for production of large amounts of the novel PDGF receptor protein.

This invention further comprises novel bioassay methods for detecting the expression of genes related to DNAs of the invention. According to one such embodiment, DNAs of this invention may be used as probes to determine levels of related mRNAs. This embodiment is exemplified by the comparison of mRNA species of the T11 and known PDGF-R genes in normal and tumor cells (FIG. 6). Total or polyadenylated RNA was separated by denaturing gel electrophoresis in formaldehyde (48), transferred to nitrocellulose, and hybridized Under stringent conditions with $^{32}$P-labeled probes. The probes were prepared from any of the following DNAs of this invention: clone pT11-HP (0.95-kbp HindIII-PstI fragment of genomic clone T11); or from T11 cDNA (3.5-kbp BamHI fragment of TR4, including the whole coding region).

Therefore, by employing the DNAs and RNAs of the invention in known hybridization methods, especially the most preferred DNAs listed herein, those skilled in the art, without undue experimentation, can measure levels of expression of type α PDGF-R gene without interference from mRNA of type β PDGF-R gene or other related oncogenes.

This invention also comprises novel antibodies made against a peptide encoded by a DNA segment of the invention or by other related DNAs. This embodiment of the invention is exemplified by rabbit antisera containing antibodies which specifically bind to type α PDGF-R protein or, in the alternative, to the known PDGF-R protein, herein designated type β.

Such type specific antisera were raised to synthetic peptides representing 15 amino acid sequences from the carboxyl-terminal regions of their respective PDGF-R proteins (residues 959–973 of the type α sequence displayed in FIG. 3, and corresponding residues 967–981 of the known type β sequence, as predicted by the respective cDNA sequences). These peptides were selected to meet the following criteria: lack of sequence relatedness between the two PDGF-R types (less than 50% sequence homology); relative hydophilicity; and carboxyl-terminal location which is known to be associated with a higher likelihood of producing antibodies reactive with native proteins.

Antisera to peptides were prepared by chemically synthesizing the peptides, conjugating them to carrier (thyroglobulin), and injecting the conjugated peptides into rabbits with complete Freund's adjuvant, according to standard methods of peptide immunization.

These antibodies can be used for detection or purification of the protein products. Thus, FIG. 7 shows the use in Western blot experiments of two different rabbit antibodies [anti-T11 (PDGF-R type α) and anti-HPR (PDGF-R type β)] raised against the corresponding type-specific peptides. As is evident from the figure, the appropriate PDGF-R types are specifically detected in various cells by antisera from rabbits immunized with synthetic peptides.

EXPERIMENTAL SECTION

This section describes experimental work leading to the identification and cloning of a genomic sequence and cDNAs of a novel receptor-like gene of the PDGF receptor/CSF-1 receptor subfamily. The gene gives rise to a 6.4-kb RNA transcript that is coexpressed in normal human tissues with the known 5.3-kb PDGF receptor mRNA. The new PDGF receptor gene was localized to chromosome 4 at location 4q 11–12, consistent with the clustering of other genes of this receptor subfamily on ancestrally related chromosomes 4 and 5.

That the cloned cDNA is functional is demonstrated by the observation that introduction (by transfection using a viral vector) of a cDNA of the novel gene into COS-1 cells leads to expression of proteins which are specifically detected with anti-serum directed against a predicted peptide. Transfected but not control COS-1 cells demonstrate specific binding of $^{125}$I-human PDGF, which is efficiently competed by all three PDGF isoforms, including the main AB form found in human platelets. In contrast, expression of the known PDGF receptor cDNA in COS-1 cells leads to PDGF binding with a distinct pattern of competition by the same PDGF isoforms characterized by a marked preference for PDGF form BB Further evidence that the new receptor gene encodes a distinct PDGF receptor derives from examination of human cells, originally free of PDGF receptors, in which PDGF-receptor activities are reconstituted by either type α or type β receptors introduced by transfection with vectors bearing the respective cDNAs. Cells with the type α receptors are significantly more responsive to PDGF-AB in all of the following PDGF-mediated cellular activities: tyrosine phosphorylation of the receptor gene product; stimulation of DNA synthesis and consequent cell proliferation; chemotaxis; phosphoinositide breakdown; and cytosolic calcium mobilization ([$Ca^{2+}$]i).

Thus, while each type of reconstituted PDGF-R gene product independently elicits similar biochemical as well as biological responses to PDGF-BB, the type α PDGF-R is the preferred receptor for PDGF-AB, the principal isoform of human PDGF which is found in platelets. Accordingly, it follows that abnormalities in the structure or expression of the type α PDGF receptor could have profound pathological effects for which the present invention provides means of diagnosis and therapy.

MATERIALS AND METHODS

Detection of v-fms and PDGF receptor-related gene fragments in human placenta and thymus DNAs. Genomic DNA (20 μg) was digested with EcoRI, separated by electrophoresis in 0.8% agarose gels, and transferred to nitrocellulose paper (41). Hybridization to $^{32}$P-labeled probes (42) was conducted in a solution of 50% or 30% formamide, 0.75 M NaCl, and 0.075 M sodium citrate, at 42° C. (43). After hybridization, the blots were washed in 2×SSC (0.3 M NaCl; 0.03 M sodium citrate) at room temperature, and then in 0.1× or 0.6×SSC at 50° C. (stringent or relaxed condition, respectively). The v-fms probe was a 0.44-kbp XhoI-BglII fragment encompassing nucleotides 3891 to 4419 of the v-fms oncogene (44). The mouse PDGF receptor probe was a 0.5-kbp SinI-PvuI fragment encompassing nucleotide 2490 to 2995 of its cDNA (6).

Molecular cloning of the λT11 genomic fragment as well as cDNAs of T11 and PDGF-R genes. Libraries from which specific cDNA clones (in parentheses) were isolated included: human fibroblast mRNAs in the Okayama-Berg vector (pHF); human infant brain mRNAs in λgt11 (λHB); human embryonic fibroblast random primed mRNAs in λgt11 (λEF); and human embryonic fibroblast mRNAs in the directional cloning phagemid (TR4 or HPR). Restriction sites were determined by electrophoretic analysis of the products of single and double digestions. Regions of λT11 homologous to the v-fms or mouse PDGF receptor probes were identified by hybridization as described in FIG. 1. Three restriction fragments (0.95-kbp HindIII-PstI, 0.5-kbp AvaI-SacI, and 0.35-kbp KpnI-XbaI) including regions homologous to the v-fms and mouse PDGF receptor probes were subcloned into plasmids and sequenced by the dideoxy chain termination method (45).

Chromosome mapping of the T11 gene. The probe was labeled with all four $^3$H-nucleotides (New England Nuclear, Boston, Mass.) using a modified nick translation kit (Amersham, Arlington Heights, Ill.) to a specific activity of 2.5×10$^7$ cpm/µg DNA. In situ hybridization with human metaphases and prometaphases from methotrexate-synchronized peripheral lymphocyte cultures was carried out as previously described (47).

Comparison of mRNA species by Northern blot hybridization. Total or polyadenylated RNA was separated by denaturing gel electrophoresis in formaldehyde (48), transferred to nitrocellulose, and hybridized under stringent conditions (50% formamide, 0.075M NaCl, 0.75M sodium citrate, at 42° C.) with $^{32}$P-labeled probes.

Detection of T11 and PDGF-R proteins with peptide antisera. Anti-T11 and anti-PDGF-R sera were obtained following immunization of rabbits with 15 amino acid peptides from the corresponding carboxyl-terminal regions of the predicted receptors. These peptide sequences were less than 50% homologous. cDNA expression plasmids were constructed by introducing the T11 cDNA encompassing nucleotides 1 to 3454 (FIG. 3) or the PDGF-R cDNA encompassing nucleotides 1 to 3939 into the pSV2 gpt vector into which the simian sarcoma virus LTR had been engineered as the promoter (49). About 10$^6$ COS-1 cells in 10 cm petri dishes were incubated in Dulbecco's modified Eagle's medium (DMEM) supplemented with 10% fetal calf serum 24 hr prior to transfection. DNA transfection was performed by the calcium phosphate precipitation method (50) 48 hours prior to analysis. Cultures were lysed with staph-A buffer (10 mM sodium phosphate pH 7.5, 100 mM NaCl, 1% Triton X-100, 0.1% SDS, 0.5% deoxycholate, 0.1% aprotinin, 1 mM PMSF, and 1 mM sodium orthovanadate) and clarified by centrifugation at 10,000×g for 30 min. Proteins (100 µg per lane) were resolved by electrophoresis in 7% SDS-polyacrylamide gels, transferred to nitrocellulose filters and probed by immunoblot analysis (with or without peptide blocking) using $^{125}$I-Protein A (51).

Binding of $^{125}$I-labeled human PDGF to receptors on cells. COS-1 cells were plated in 12-well plates and trans-fected 48 hours before assay as described in FIG. 7. Human PDGF was labeled with $^{125}$I by the chloramine-T method to specific activities of 3.7×10$^4$ cpm/ng (52). The binding of $^{125}$I-labeled PDGF isolated from human platelets (53) in the absence or presence of a 50–100 fold excess of unlabeled human PDGF (AB) (Collaborative Research), recombinant PDGF-BB (AmGen) or recombinant PDGF-AA (37), was carried out at 4° C. for 2 hrs. Unbound $^{125}$I-PDGF was removed by four successive washes with binding buffer (DMEM containing 1 mg per ml bovine serum albumin). The cells were then lysed in solubilizing buffer (1% Triton X-100, 20 mM Hepes pH 7.4, 10% [v/v] glycerol), and radioactivity measured with a τ counter.

Tyrosine autophosphorylation of type α and type β PDGF-R gene products. After incubation with PDGF for 5 min at 37° C., cell lysates were immunoprecipitated with anti-peptide antisera. Total cell lysates or immunoprecipitates were analyzed by immunoblotting with antibodies to the receptors or to phosphotyrosine (anti-P-Tyr) (54). The anti-phosphotyrosine antibodies were preincubated with 10 mM phosphotyrosine for blocking.

RESULTS

Detection of a novel human PDGF-R/CSF1R-related gene. In order to explore novel sequences related to known growth factor receptor genes of the PDGF-R/CSF1-R family, high molecular weight DNAs prepared from human placenta and thymus were digested with EcoRI and analyzed by blot hybridization with DNA probes derived from the tyrosine-kinase domains of v-fms and the mouse PDGF-R gene (FIG. 1). Under stringent conditions, the v-fms probe detected EcoRI restriction fragments of 27-kbp and/or 20-kbp, due to the previously reported restriction polymorphism at this locus (8). Under less stringent conditions, several additional fragments of 12-, 6.8-, 5-, 2.7-, 2.2-kbp, which hybridized to the v-fms probe, were observed. The corresponding region of the mouse PDGF-R cDNA hybridized with a single 21-kbp fragment under stringent conditions (FIG. 1).

At lower stringency, the same probe detected several additional fragments, some of which had sizes similar to those of the v-fms-related fragments described above. Among these, the 12-kbp EcoRI fragment hybridized more strongly than the other fragments with both probes. Moreover, some of the smaller bands corresponded to restriction fragments reported for human c-kit (7). Thus, it was decided to clone the 12-kbp EcoRI DNA fragment and characterize it more fully.

Using the λEMBL-4 vector system, a genomic library size-selected by sucrose gradients was constructed from EcoRI-digested normal human thymus DNA. FIG. 2 shows the restriction map of λT11 containing a 12-kbp EcoRI insert, which hybridized with both v-fms and mouse PDGF-R probes only under relaxed but not stringent hybridization conditions. Regions homologous to v-fms/PDGF-R tyrosine kinase domains were localized by hybridization to restriction endonuclease digests of λT11 DNA.

Three plasmid subclones containing sequences hybridizing to the 0.95-kbp HindIII-PstI, 0.5-kbp AvaI-SacI, and 0.35-kbp KpnI-XbaI fragments of λT11 were subjected to nucleotide sequence analysis. Their discrete open reading frames (FIG. 3) showed relatedness to both human c-fms and mouse PDGF-R genes, but were readily distinguished from each of these genes (3,6) as well as from c-kit (7). The three putative coding regions were each flanked by the AG and GT dinucleotides that border the exons of eukaryotic genes (9).

To assess whether the T11 sequence was transcribed, Northern blot analyses of a variety of cells were performed using a clone of the 0.95-kbp HindIII-PstI fragment (pT11-HP) which contained exon (a) (FIG. 2) and lacked human repetitive sequences. Under stringent conditions, a single 6.4-kb RNA transcript was detected in poly(A)+ RNA prepared from normal human fibroblasts (data not shown). This transcript differed in size from previously reported transcripts for the PDGF-R (6), c-fms (3) or c-kit genes (7). All of these findings indicated that the T11 sequence represented a gene distinct from known members of this subfamily of tyrosine kinase receptors.

cDNA cloning of the novel gene. A normal human fibroblast cDNA library in the Okayama-Berg expression vector was initially screened under stringent conditions using the pT11-HP clone of the 0.9-kbp HindIII-PstI fragment of λT11. One strongly hybridizing clone containing a 3.9-kbp cDNA insert was isolated (FIG. 2). This clone, designated pHF1, hybridized to a 6.4-kb transcript in normal human fibroblasts and contained a polyadenylation signal followed by a poly(A) tail at its 3' end. It also contained the coding sequence within the λT11 DNA and 170 nucleotides related to CSF1-R-PDGF-R tyrosine kinase domains upstream of exon (a).

The 0.4-kbp 5' end of pHF1 was used to search for overlapping cDNA clones in a human infant brain library. Under stringent conditions, a number of positive clones with similar restriction maps were isolated (data not shown). The longest, λHB6, (FIG. 2) was subjected to sequence analysis. A possible ATG initiation codon was identified within another clone, λEF17, isolated by screening a M426 human embryo fibroblast cDNA library in the λgt11 vector with a 0.2-kbp 5' fragment of λHB6 as a probe. The three overlapping clones (pHF1, λHB6 and λEF17) contained the entire coding region in addition to 138-bp 5' and ˜3-kbp of 3' untranslated sequences (FIG. 2).

Two clones, λHB3 and λHB4, that gave weaker signals in plaque hybridization during screening of the human infant brain library were also sequenced. These showed close similarity to the sequence of the mouse PDGF-R cDNA (6). Moreover, when the 2.0-kbp insert of λHB4 was hybridized to normal human fibroblast RNA, it detected a transcript of 5.3-kb, consistent with that of the PDGF-R (6).

No clones containing sequences further upstream from the 5' end of λHB4 could be obtained by screening the human infant brain cDNA library in λgt11. This was accomplished by utilizing a M426 human embryo fibroblast cDNA library in a new phagemid vector constructed as described elsewhere (10). By screening this library with a 0.3-kbp 5' subfragment of λHB3, two overlapping clones, HPR2 and HPR5, were obtained. These contained between them the entire known human PDGF-R coding sequence, its complete 3' untranslated region, and 360 nucleotides of its 5' untranslated region (FIG. 2). A 6.4-kbp cDNA clone (TR4) of the novel related gene was also obtained from this same library by screening with a 5' 0.2-kbp subfragment of λEF17.

Deduced amino acid sequence establishes the T11 gene as a member of the PDGF-R/CSF1-R subfamily. The complete nucleotide sequence of the 6.4-kbp cDNA of the T11 gene is shown in FIG. 3. An open reading frame beginning with a possible ATG initiation codon at nucleotide position 139 extended to a TAA termination codon at position 3406. Although the open reading frame extended further upstream, the putative initiation ATG was flanked by sequences that fulfill the Kozak criteria for an authentic initiation codon (11). Moreover, the first 23 amino acid stretch displayed properties of a cleavable hydrophobic signal peptide (FIG. 3 & 4). At the 3' end, the open reading frame was followed by ˜3-kbp of untranslated sequences. A polyadenylation signal (AATAAA) was located 25 nucleotides upstream from the poly(A) sequence at the 3' end of the cDNA.

According to the putative cleavage site for the signal peptide (12), the amino terminus of the mature product was predicted to be glutamine at amino acid 24 followed by 1066 amino acids. This polypeptide sequence with a calculated molecular mass of around 120 kd contained all of the characteristics of a membrane-spanning tyrosine kinase receptor. A hydrophobic segment consisting of 24 amino acids (residues 525 to 548) exhibited characteristics of a receptor transmembrane domain (FIGS. 3 & 4). Between the signal peptide and the transmembrane domain, there was structural homology with the extracellular ligand binding domains of the PDGF-R/CSF1-R subfamily. Ten cysteine residues were spaced at the same positions as in the other receptors of this subfamily, and eight potential N-linked glycosylation sites were distributed in its putative extracellular domain (FIG. 3).

The cytoplasmic domain was comprised of a conserved tyrosine kinase region and a hydrophilic carboxyl-terminal tail (FIGS. 3 & 4). The tyrosine kinase domain included the consensus ATP binding sequence (residues Gly-X-Gly-X-X-Gly . . . Lys) and a tyrosine residue at position 849 homologous to the major autophosphorylation site of pp60$^{v\text{-}src}$ at position 416 (13). Moreover, the tyrosine kinase was divided into two domains by a hydrophilic inter-kinase sequence as previously shown for c-fms/CSF1-R, PDGF-R, and c-kit (FIG. 4).

The amino acid homologies of its extracellular domain with those of the PDGF-R, CSF1-R, and c-kit were 31%, 18%, and 19% respectively. The two kinase domains of the T11 gene were most homologous to those of the human PDGF receptor (85% and 75%, respectively) as compared with 67 to 70% for c-fms and c-kit (FIG. 4). Even in the inter-kinase domain, its amino acid sequence was more closely aligned to the PDGF-R with 27% homology compared to 10 and 19% with c-fms or c-kit. These observations lead to the conclusion that the T11 product was in the PDGF-R/CSF1-R subfamily and most closely related to the PDGF-R.

The deduced amino acid sequence of another cDNA clone (obtained in the same experiment which produced the TR4 cDNA clone) established its product as the known human PDGF receptor. Its sequence corresponded almost completely with the recently published sequence of the known human PDGF receptor (14). A single nucleotide difference changed residue 240 from Asn to Ser. Comparison with the mouse PDGF receptor cDNA amino acid sequence also revealed high similarities throughout all functional domains including the ligand binding domain (79%), transmembrane domain (96%), the juxtamembrane domain (97%), split tyrosine kinase domains (TK1, 99% and TK2, 97%), inter-kinase domain (86%) and carboxyl terminus (85%).

Chromosomal mapping of the T11 gene. To define the new gene with respect to chromosomal location, 104 chromosome spreads were examined by in situ hybridization with a pT11-P probe. A total of 136 grains were localized on a 400-band ideogram (FIG. 5). Of the total grains, 50 (37%) were on chromosome 4 with the majority of 45 grains tightly clustered near the acentromeric region of the long arm at bands, q11–12 (FIG. 5). A second site of hybridization on chromosome 5q 11.1–11.2 consisting of 7 grains accounted for 5% of the total grains (FIG. 5).

The T11 gene probe was also hybridized to chromosomes derived from a Burkitt lymphoma cell line carrying a large abnormal marker chromosome originating from a translocation t1;5 (p22; q23) translocation. There was no detectable labeling of the rearranged chromosome 5 in over 300 spreads examined for the presence of grains at this chromosome. Thus, in situ hybridization assigned the T11 gene to chromosome 4 at location q 11–12. This localization places the new gene within the same region as the c-kit proto-oncogene (15). The structurally related genes for platelet factor 4, (16), interferon τ-inducible factor; τIP-10, (17) and melanoma growth stimulatory activity (MGSA) (18) as well as genes for α-feto protein, albumin (19), HPAFP (20), and the gene for dentinogenesis imperfecta have been mapped at 4q 11–13 (21).

Expression of transcripts and protein products of the endogenous T11 gene in normal and tumor cells. To investigate the tissue specific expression of the new receptor-like gene, either of the most preferred DNAs of this invention, i.e., the HindIII-PstI 0.95-kbp fragment of the T11 genomic clone, or cDNA insert of TR4, was used for Northern blot hybridization experiments. A single 6.4-kb transcript was detected in poly(A)-containing RNAs of a variety of human tissues and cell lines. As shown in FIG. 6, relatively high levels of the transcript were found in smooth muscle, heart, and human embryo, while human liver and spleen demonstrated undetectable or barely detectable transcripts under these conditions.

Using a probe for the known human PDGF receptor gene, it was noted that the T11 and 5.3-kb PDGF-R transcripts appeared to be coexpressed at similar respective levels in each of these same tissues. Human skeletal muscle, fetal brain, placenta as well as cultured fibroblasts and glial cells also expressed high levels of both transcripts (data not shown).

Thus, the new gene and the known PDGF-R gene appeared to be coordinately expressed in normal tissues examined and exhibited a very different pattern from that reported for either c-fms/CSF1-R or c-kit (3,7).

Expression of the T11 and PDGF-R genes were also compared in human tumor cells. Here, their patterns of expression could be readily distinguished. Several tumor cell lines were found to contain one or the other transcript but not both (FIGS. 6C and D).

Antibodies specific for either the novel or known PDGF receptor protein. In an effort to identify the protein product of the new gene, antisera to peptides were prepared based on its predicted sequence. Analogous regions of the predicted sequence of the known PDGF-R were utilized to generate antisera as well. Initial efforts to detect specific expression of the T11 gene product utilized M426 embryo fibroblast cells, from which cDNAs of both receptors had been isolated. 8387 and A204 cell lines which specifically expressed the PDGF-R or T11 gene transcripts, respectively were analyzed as well (FIG. 7A).

Western blot analysis of M426 cells with antisera (anti-T11) directed against the T11 gene product revealed 180 kd and 160 kd protein species, which were specifically competed by the immunizing peptide. The anti-PDGF-R peptide serum (designated anti-HPR) detected 180 and 165 kd proteins in the same cells. Western blot analysis of 8387 cells revealed 180 and 165 kd species, which were recognized by the anti-HPR, but not by anti-T11 serum. Conversely, A204 cells contained 180 and 160 kd species which were specifically detected by anti-T11, but not recognized by anti-HPR serum.

All of these findings indicated that these antibodies of this invention were specific for detection of the homologous receptor gene product and that T11 gene products were expressed in cells containing its transcript.

Expression of T11 cDNA in a mammalian vector system. As further test of the ability to immunologically detect the T11 gene product as well as to investigate the functional expression of its cDNA, LTR-based expression vectors were constructed for the T11 cDNA encompassing nucleotides 1 to 3454 (FIG. 3) and for the corresponding known PDGF-R cDNA as well.

Transient expression in COS-1 cells led to the specific detection of the T11 gene products as 185 kd and 160 kd species (FIG. 7B) whereas the PDGF-R appeared as 185 kd and 165 kd proteins. The respective lower MW forms of each receptor did not vary in size among the cells analyzed. However, some different sizes of the higher MW species were observed, which were likely due to cell specific differences in glycosylation.

PDGF binding to the T11 product establishes it as a new PDGF-R gene. Because of their structural and deduced amino acid sequence similarities as well as their coexpression by normal cell types known to respond to PDGF, to studies were performed to determine whether the T11 gene product exhibited any functional relationship to the known PDGF-R gene product. Thus, $^{125}$I-labeled human PDGF was incubated with control and transfected COS-1 cells in the presence or absence of unlabeled PDGF isoforms.

As shown in FIG. 8, as much $^{125}$I-PDGF specifically bound to COS-1 cells transfected with the new receptor gene as to NIH/3T3 cells. Binding was reduced to the level of nontransfected COS-1 cells by competition with excess human PDGF (predominantly AB), PDGF-BB, or PDGF-AA. Specific binding of $^{125}$I-PDGF to COS-1 cells transfected with the PDGF-R cDNA was also observed. In this case, however, binding was competed by human PDGF (i.e., PDGF-AB) and PDGF-BB but not by PDGF-AA (FIG. 8).

Thus, while both T11 gene and PDGF-R gene products bound human PDGF, the pattern of competition by different PDGF isoforms distinguished the two receptors. These results implied that the T11 gene encoded a novel PDGF receptor with different affinities for the three dimeric forms of PDGF. Hence, the T11 receptor gene product was tentatively designated as the type α PDGF-R because PDGF binding was competed by AA as well as BB isoforms, and the product of the previously cloned PDGF receptor was designated as type β.

PDGF isoforms induce different patterns of autophosphorylation of the novel and known PDGF receptors. After PDGF binding to its receptor, a number of molecular events are rapidly triggered in vivo, including phosphorylation of the receptor protein on tyrosine residues (22). To compare the relative autophosphorylation of the products of the two PDGF-R genes by each PDGF isoform, the responses of A204 and 8387 cells that expressed type α and type β PDGF-R genes, respectively, were analyzed.

As shown in FIG. 9A, immunoblots of A204 cells lysed 5 minutes following ligand exposure revealed readily detectable and very similar levels of autophosphorylation of a 180 kd species in response to each of the three PDGF isoforms. As further evidence that the induced autophosphorylation was specific to the type α receptor gene product, ligand stimulated A204 cell lysates were first subjected to immunoprecipitation with anti-type α PDGF-R serum (anti-T11) followed by immunoblotting with anti-phosphotyrosine serum. By this approach, it was firmly establish that the 180 kd type α PDGF receptor was phosphorylated on its tyrosine with similar intensity in response to each of the three ligands.

Exposure of 8387 cells, which expressed only the type β PDGF gene product, to the same amount of each respective PDGF isoform revealed a very different pattern of receptor autophosphorylation. Here, PDGF-BB induced the highest level of autophosphorylation of the 180 kd species specifically recognized by anti-type β PDGF-R serum (anti-HPR), and human PDGF induced detectable autophosphorylation as well (FIG. 9B). In contrast, PDGF-AA induced no detectable phosphorylation.

Thus, while PDGF-AB and PDGF-BB triggered both receptors, the much stronger response of the β type receptor to the BB homodimer as well as its lack of detectable response to the AA homodimer readily distinguished the receptors functionally.

To investigate the pattern of autophosphorylation of the two receptors by different PDGF isoforms in the same cells, NIH/3T3 cells were first triggered by different ligands followed by immunoprecipitation with either anti-type α or β PDGF-R serum. The immunoprecipitated receptor proteins were then analyzed by immunoblotting with anti-phosphotyrosine serum.

As shown in FIG. 9C, the 180 kd protein immunoprecipitated by the type α PDGF-R antiserum was phosphorylated by all three dimeric forms of PDGF. In contrast, the 180 kd phosphoprotein immunoprecipitated by the anti-type β receptor serum was detected only after human PDGF-AB or PDGF-BB stimulation. Thus, the patterns of response to different PDGF ligands remained receptor-specific in at one example of nontransformed cells naturally expressing both PDGF-R genes.

Type α PDGF receptor is more efficient in stimulating DNA synthesis in response to PDGF isoform AB. The expression of the two receptors in other fibroblast lines was analyzed next. Western blotting analysis (data not shown) revealed significant variations in the ratio of the two receptors among the lines analyzed. Whereas mouse fibroblasts expressed similar levels of type α and type β receptors, human fibroblasts such as AG1523 or M413 expressed relatively lower levels of the type α receptor than either mouse fibroblasts or M426 human fibroblasts.

Saturating amounts of PDGF-AB or PDGF-BB yielded similar increases in DNA synthesis in each of the cell lines (data not shown). However, submaximal doses of PDGF-AB and PDGF-BB showed significant differences in the levels of mitogenic activity observed (FIG. 10). Whereas, NIH/3T3, BALB/3T3 and M426 cells responded with comparable efficiency to PDGF-BB and AB, PDGF-AB was significantly less active on AG1523 or M413 cells. Their lesser mitogenic responsiveness to PDGF-AB seemed to correlate with the high ratio of β to α receptors in these cells detected immunologically.

Taken together with the dose-response curves observed for phosphorylation of the two receptors in NIH/3T3 cells by the different PDGF isoforms, these results strongly suggested preferential triggering of the type α receptor, in the presence of the type β receptor by PDGF-AB, as well as by PDGF-AA.

Independent expression of two PDGF gene types after introduction of cDNAs into PDGF receptor-free hematopoietic cells. To investigate the biological and biochemical responses specific to each PDGF-R gene product, systems were developed to look at this receptor in cells in which each type could be independently introduced and expressed. These systems were based on the 32D cell line, a mouse hematopoietic cell line normally dependent on Il-3 for survival and proliferation. Recent studies have established that introduction of an expression vector for the EGF-R in these cells led to effective coupling with EGF mitogenic signal transduction pathways.

The mammalian expression vectors described above, carrying the gpt selectable marker, was used to transfect 32D cells with either the type α or the type β PDGF-R cDNAs by electroporation. Transformants were selected using medium supplemented with mycophenolic acid. After 2 weeks in the selective medium, viable cultures were obtained.

Cultures designated 32D-αR and 32D-βR, respectively were subjected to Northern blot analysis, as described above. Neither type of PDGF-R mRNA was detectable in the parental 32D cells even under relaxed hybridization conditions, which conditions enabled detection of the respective mouse PDGF-R gene transcripts in NIH/3T3 fibroblasts. In contrast, 32-αR and 32-βR transfectants expressed abundant transcripts specific to the human type α and type β PDGF-R genes, respectively. When membranes lysates of these transfectant were subjected to immunoblot analysis, anti-type α PDGF-R peptide serum detected 180 kd and 160 kd protein species in 32D-αR but not in 32D-β cells. Moreover, these proteins were specifically competed by the immunizing peptide. Conversely, 32D-βR cells contained 180–200 kd and a 165 kd species which were specifically detected by the anti-type β PDGF-R serum. None of these proteins species were detectable in control 32D cells.

Type α receptor has a higher binding affinity for the PDGF-AB isoform. PDGF-BB binding was compared in 32D-αR or 32D-βR transfectants, and both showed high affinity binding. Scatchard analysis revealed about two thousand receptors per cell with a single affinity class of binding sites. The $K_d$s were 0.4 nM and 0.5 nM for 32D-αR and 32D-βR cells, respectively (FIG. 11). 32D-αR cells also showed a high binding affinity ($K_d$=0.4 nM) for $^{125}$I-PDGF-AB, exhibiting the same number of binding sites as for PDGF-BB.

In contrast, however, 32D-βR cells revealed ten times less binding capacity for $^{125}$I-PDGF-AB than did 32D-αR cells. Thus, standardized on the basis of their similar binding of PDGF-BB, the type β receptor showed a strikingly lower affinity for PDGF-AB.

Common biological functions independently triggered by type α and β PDGF gene products. Mitogenesis and chemotaxis are among the most well characterized responses of fibroblasts to PDGF. Thus, whether 32D-αR or βR lines mediated either of these biological responses was investigated.

Growth of 32D cells is normally strictly dependent on IL-3, and deprivation of IL-3 from the medium led to the rapid loss of viability both of the transfectants and the control 32D cells. As shown in FIG. 12, PDGF-BB was able to couple efficiently with mitogenic signal transduction pathways and abrogate IL-3 dependence in a similar does dependent manner in both transfectants, but had no effect in control 32D cells. Thus, the presence of either type α or β PDGF-R was both necessary and sufficient for the mitogenic response to PDGF BB.

However, whereas, the type α receptor containing 32D cells were as responsive to PDGF-AB as to PDGF-BB, PDGF-AB elicited a significantly lesser DNA synthesis response in 32D-βR cells (FIG. 12).

These findings were confirmed by analysis of colony-formation in semi-solid agar containing medium. Both transfectants formed colonies readily in PDGF-BB, supplemented medium but only 32D-αR cells did so in medium supplemented with PDGF-AB (data not shown). Thus, the mitogenic responses observed with both 32D-αR and βR transfectants correlated well with the binding properties of the same PDGF isoforms to α and β receptors expressed by each cell line, respectively.

To address whether chemotaxis was specifically mediated by either type α or β PDGF receptors, a chemotaxis assay was employed using the modified Boyden chamber technique well known in the art. While 32D cells lacking PDGF receptors did not respond to PDGF-AB or PDGF-BB, PDGF-BB was chemotaxic for both α and β receptor expressing transfectants. PDGF-AB was relatively more active on 32D-αR cells (FIG. 13).

Thus, each PDGF receptor independently coupled with both mitogenic and chemotaxis signalling pathways inherently present in 32D cells. Moreover, these biological functions were triggered according to the relative binding abilities of PDGF isoforms to either receptor.

Inositol lipid metabolism and cytosolic $Ca^{2+}$ mobilization coupling with independently reconstituted receptors. Recent investigations have suggested an important role of receptor-mediated turnover of inositol lipids resulting in the increase of second messengers such as intracellular free calcium and diacyloglycerol in the transduction of the PDGF-induced mitogenic signal. Thus, the effects of PDGF-AB and PDGF-BB on inositol lipid metabolism and intracellular free $Ca^{2+}$ ($[Ca^{2+}]i$) were studied in type α and type β PDGF-R containing 32D cells.

The accumulation of radioactive inositol phosphates was measured after prelabelling cultures with $^3$H-myoinositol and challenge with PDGF isoforms at 37° C. in the presence of LiCl, according to methods well known in the art. $[Ca^{2+}]i$ was measured in 32D cells in suspension, loaded with the fluorescent $[Ca^{2+}]i$ indicator fura-2, and treated with PDGFs in the complete incubation medium.

FIG. 14 shows the effect of PDGF-AB and PDGF-BB on inositol phosphate formation and $[Ca^{2+}]i$ in type α and type β PDGF-R 32D cells. As shown in FIG. 14 (panel A), both PDGF-BB and PDGF-AB were able to elicit dose-dependent accumulation of inositol phosphates, with similar relative potencies. The same isoforms exerted almost identical increases in $[Ca^{2+}]i$ in type α PDGF-R 32D cells as wells (FIG. 14, panel A, insert). PDGF-BB also markedly stimulated inositol lipid metabolism and intracellular $Ca^{2+}$ mobilization in type β PDGF-R 32D cells, establishing the very similar biochemical responses elicited by these distinct PDGF-R gene products in 32D cells in response to PDGF-BB.

FIG. 14 (panel B) shows that PDGF-AB was significantly less effective than PDGF-BB in promoting inositol phosphate accumulation in type β PDGF-R 32D cells. Detectable release of inositol phosphate occurred only at high PDGF-AB concentration. Similarly, PDGF-AB elicited little or no $(Ca^{2+})i$ response.

DISCUSSION

The present studies demonstrate the existence of two distinct human PDGF receptor genes. Further, they illustrate the detection and isolation of two principal embodiments of this invention, the genomic and cDNA clones of a novel gene within the PDGF-R/CSF1-R subfamily. This gene is divergent from but most closely related to the known PDGF-R gene. Under conditions of natural expression as well as following introduction of this novel cDNA into appropriate target cells by means of an expression vector, functional responses of its product to PDGF were demonstrated at concentrations that bound and triggered tyrosine phosphorylation of the previously identified PDGF receptor.

Standardized on the basis of similar levels of tyrosine phosphorylation (and several other activities) of PDGF-R gene product induced by a constant amount of PDGF, the new receptor was shown to respond better than the known PDGF-R to the AA homodimer. Conversely, the known receptor responded preferentially to the BB homodimer. Based upon the present findings, the new gene product has been designated as the type α PDGF-R and the previously identified PDGF-R gene product as the type β receptor.

The AA homodimer failed to stimulate detectable tyrosine phosphorylation of the β type receptor in NIH/3T3 cells and yet is capable of inducing DNA synthesis in this cell line (37). This indicated that the α type receptor can couple with mitogenic signalling pathways in fibroblasts. The β type receptor has also been reported to couple PDGF with mitogenic pathways (28). These results suggested that both receptor gene products can induce a proliferative response.

The ability, according to compositions and methods of this invention, to stably introduce expression vectors for these distinct receptor genes into a null cell made it possible to confirm this suggestion in human cells. Further studies in such cells showed that other known PDGF functions including chemotaxis (38), membrane ruffling (39), as well as transmodulation of a heterologous receptor (40), are not specifically mediated by either type α or β PDGF-R gene products.

Such knowledge is a necessary prelude to understanding and diagnosis of disease conditions affecting these PDGF functions, which can be furthered through additional practice of the present invention.

Among human tumor cell lines analyzed using methods of this invention, several were observed in which there was discoordinate expression of the two PDGF-R genes. Moreover, representative tumor cell lines expressing mRNA from either gene were shown to contain the respective protein product, which bound and was phosphorylated on tyrosine in response to PDGF.

The availability of the immunologic as well as the molecular probes of this invention, specific for either type α or type β PDGF-R gene products, makes it possible to identify human tumors in which expression of the PDGF-A or B chain, in combination with either receptor gene, may be causally implicated in tumor development. At the same time, the availability of reagents for specific detection of each type of component is a critical aid in efforts to implicate the abnormal expression of this complex growth factor-receptor network in other chronic disease states such as arteriosclerosis, arthritis, and fibrotic diseases (23)

Additional observations of scientific import have already been provided by the practice of the invention as herein described. For instance, the chromosomal location of the novel gene, established using DNAs of this invention, provides insight into the possible evolution of this receptor gene family. Thus, the chromosomal localization places the type α PDGF receptor gene on chromosome 4 at 4q 11–12, the same region as c-kit (15), a related receptor-like gene. Other genes of this subfamily have been localized on chromosome 5. These include the type β PDGF-R mapped at 5q 23–31 (6) and the CSF1-R gene, on 5q 33.2–33.3 (29). There is evidence for a common ancestral origin of human chromosomes 4 and 5 (30). These related receptor genes cluster near the centromere on 4q or at the distal half of 5q.

Thus, if the progenitor(s) of these genes were confined to a single ancestral chromosome, the breakup of linkage might be explained by an inversion within the long arm.

The present studies also establish that different PDGF-R genes encode two receptor types, with binding properties evidently independent of the cell in which each is expressed. The implications of this observation can be better appreciated in light of knowledge about other receptor systems.

There is emerging evidence that as more complex organisms have evolved, mechanisms of intercellular communication have increased in complexity as well. The related EGF and TGF$_\alpha$ molecules interact with similar affinities with a common receptor, the EGF receptor (31). Different patterns of developmental and tissue expression of these growth factors (32) presumably account for their present existence.

There are increasing examples of evolutionarily divergent receptor genes as well. The products of such genes can respond to completely different ligands, as is the case of PDGF and CSF-1 receptors (33,34), or, alternatively, to related ligands, as with the IGF-I and insulin receptors (35). Here the developmental and tissue specific expression of both the receptors and their ligands, as well as the biochemical responses triggered, have evolved with the complexity of the organism.

As demonstrated in the present studies, the responses mediated by PDGF not only involve different dimeric forms of the related ligands encoded by two genes, but two related genes encoding different PDGF receptors as well. In addition to their differences in tissue specific expression (34,36), the two PDGF gene products are known to differ in their relative secretory capacity. The PDGF-A chain is much more efficiently released than is the B chain (37), giving the former the possibility of acting at greater distances.

In view of the present evidence of coordinate expression of the two PDGF receptor genes in all normal tissues so far examined, their tissue specific expression may not be a major determinant of their functions. However, application of the methods of the present invention to a comprehensive survey of the expression of each receptor type during embryonic development and in homogeneous normal cell populations may uncover evidence of differential regulation.

REFERENCES

1. R. F. Doolittle et al., Science 221, 275 (1983); M. D. Waterfield et al., Nature 304, 35 (1983); K. C. Robbins et al., ibid. 305, 605 (1983).
2. J. Downward et al., ibid. 307, 521 (1984); A. Ullrich et al., ibid. 309, 418 (1984).
3. C. J. Sherr et al., Cell 41, 665 (1985); L. Coussens et al., Nature 320, 277 (1986).
4. J. M. Bishop, Science 235, 305 (1985); R. A. Weinberg, ibid. 230, 770 (1985); S. K. Hanks, A. M. Quinn, T. Hunter, ibid. 241, 42 (1988).
5. C. R. King, M. H. Kraus, S. A. Aaronson, ibid. 229, 974 (1985); G. D. Kruh et al., ibid. 234, 1545 (1986).
6. Y. Yarden et al., Nature 323, 226 (1986).
7. P. Besmer et al., ibid. 320, 415 (1986); Y. Yarden et al., EMBO J. 6, 3341 (1987).
8. D. Q. Xu, S. Guilhot, F. Galibert, Proc. Natl. Acad. Sci. USA 82, 2862 (1985).
9. R. Breathnad and P. Chambon, Annu. Rev. Biochem. 50, 349 (1981).
10. Subject of the U.S. Patent Application entitled "Efficient Directional Cloning System", to be filed February, 1989.
11. M. Kozak, Cell 44, 283 (1986).
12. G. von Heijne, Nucleic Acids Res. 14, 4683 (1986).
13. J. E. Smart et al., Proc. Natl. Acad. Sci USA 78, 6013 (1981).
14. R. G. K. Gronwald et al., ibid. 88, 3435 (1988); L. Claesson-Welsh et al., Mol. Cell. Biol. 8, 3476 (1988).
15. L. d'Auriol et al., Hum. Genet 78, 374 (1988).
16. C. A. Griffin et al., Cytogenetic Cell Genet 45, 67 (1987).
17. A. D. Luster et al., Proc. Natl. Acad. Sci. USA 84, 2868 (1987).
18. A. Richmond et al., EMBO J. 7, 2025 (1988).
19. M. E. Harper and G. Dugaiczyk, J. Hum. Genet. 35, 565 (1983).
20. M. A. Furguson-Smith et al., Cytogenet Cell Genet 40, 628 (1985).
21. S. P. Ball, P. J. L. Cook, M. Mars, K. E. Buckton, Ann Hum. Genet 46, 35 (1982).
22. A. R. Frackelton, P. M. Tremble Jr., L. T. Williams, J. Biol. Chem. 259, 7909 (1984); T. O. Daniel et al., Proc. Natl., Acad. Sci. USA 82, 2684 (1985).
23. R. Ross, E. W. Raines, D. F. Bowen-Pope, Cell 46, 155 (1986).
24. A. Johnsson, C. -H. Heldin, B. Westermark, A. Wasteson, Biochem. Biophys. Res. Commun. 104, 66 (1982).
25. C. -H. Heldin et al., Nature 319, 511 (1986).
26. P. Stroobant and M. D. Waterfield, EMBO J. 3, 2963 (1984).
27. C. -H. Heldin et al., ibid. 7, 1387 (1988); C. E. Hart et al., Science 240, 1529 (1988).
28. J. A. Escobedo et al., ibid. 240, 1532 (1988).
29. M. M. Le Beau et al., ibid. 231, 984 (1986).
30. D. E. Comings, Nature 238, 455 (1972).
31. J. Massague, J. Biol. Chem. 258, 13614 (1983).
32. R. Derynck et al., Cancer Res. 47, 707 (1987); D. C. Lee et al., Mol. Cell. Biol. 5, 3644 (1985); D. R. Twardzik, Cancer Res. 45, 5413 (1985); R. J. Coffey et al., Nature 328, 817 (1987).
33. E. S. Kawasaki et al., Science 230 291 (1985).
34. C. Betsholtz et al., Nature 320, 695 (1986).
35. A. Ullrich et al., Nature 313 (1985); Y. Ebina et al., Cell 40, 747 (1985); A. Ullrich et al., EMBO J. 5, 2503 (1986).
36. R. A. Seifert, S. M. Schwartz, D. F. Bowen-Pope, Nature 34, 669 (1984); M. Jaye et al., Science 228, 882 (1985); J. Nilsson et al., Proc. Natl. Acad. Sci. USA 82, 4418 (1985); T. Collins et al., Nature 316, 748 (1985).
37. P. Beckman et al., Science 241, 1346 (1988).
38. H. Seppa et al., J. Cell Biol. 92, 584 (1982); G. R. Grotendorst et al., J. Cell Physiol. 113, 261 (1982); T. F. Deuel, R. M. Senior, J. S. Huang, G. L. Griffin, J. Clin. Invest. 69, 1046 (1982).
39. K. Mellstrom et al., J. Cell Motility and Muscle Res. 4, 589 (1983).
40. E. Rozengurt, M. Rodriquez-Pnena, K. A. Smith, Proc. Natl. Acad. Sci. USA 80, 7244 (1983); R. J. Davis and M. P. Czech, ibid. 82, 4080 (1985).
41. E. M. Southern, J. Med. Biol. 98, 503 (1975).
42. P. W. J. Rigby, M. Dieckerman, C. Rhodes, P. Berg ibid. 113, 237 (1977).
43. G. M. Wahl, M. Stern, G. R. Stark, Proc. Natl. Acad. Sci. USA 76, 3683 (1979).
44. A. Hampe, M. Gobet, C. J. Sherr, F. Galibert, ibid. 81, 85 (1984).
45. F. Sanger, S. Nicklen, A. R. Coulson, ibid. 74, 5463 (1977).
46. J. Kyte and R. F. Doolittle, J. Mol. Biol. 157, 105 (1982).
47. M. E. Harper and G. F. Saunders, Chromosoma (Berl.) 83, 431 (1981); N. C. Popescu et al., Cytogenet. Cell Genet 39, 73 (1985).

48. H. D. Lehrach, D. Diamond, J. M. Wozney, H. Boedtker, Biochemistry 16, 4743 (1977).
49. C. R. King, N. A. Giese, K. C. Robbins, S. A. Aaronson, Proc. Natl. Acad. Sci. USA 82, 5295 (1985).
50. M. Wigler et al., Cell 11, 223 (1977).
51. H. Towbin, T. Staehelin, J. Gordon, Proc. Natl. Acad. Sci. USA 76, 4350 (1979).
52. W. M. Hunter and F. C. Greenwood, Nature 194, 495 (1962).
53. E. W. Raines and R. Ross, J. Biol. Chem. 257, 5154 (1982).
54. J. J. Wang, Mol. Cell. Biol. 5, 3640 (1985).

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various combinations in form and detail can be made without departing from the scope of the invention.

What is claimed is:

1. An immunoassay for detection of alpha platelet-derived growth factor receptor antigen in a biological sample comprising the steps of:
   i) contacting the biological sample suspected of containing alpha platelet-derived growth factor receptor antigen with a detectable antibody composition, wherein said antibody composition consists essentially of detectable antibodies that specifically bind alpha platelet-derived growth factor receptor antigen and do not bind beta platelet-derived growth factor receptor, under conditions such that said antibodies bind to said antigen in said sample; and
   ii) detecting binding of said antibodies to said antigen in said sample, thereby detecting alpha platelet-derived growth factor receptor antigen in said biological sample.

2. The immunoassay of claim 1, wherein the antibodies are polyclonal.

3. The immunoassay of claim 1, wherein the antibodies are monoclonal.

* * * * *

UNITED STATES PATENT AND TRADEMARK OFFICE
CERTIFICATE OF CORRECTION

PATENT NO.    : 6,228,600 B1
DATED         : May 8, 2001
INVENTOR(S)   : Matsui et al.

It is certified that error appears in the above-identified patent and that said Letters Patent is hereby corrected as shown below:

Title page,
Item [63], please delete the text under the heading "Related U.S. Application Data" and substitute therefor:
-- Division of application No. 08/439,095, filed on May 11, 1995, which is a continuation of application No. 07/915,884, filed on Jul. 20, 1992, now abandoned, which is a continuation of application No. 07/308,282, filed on Feb. 9, 1989, now abandoned. --

Item [56], References Cited, OTHER PUBLICATIONS,
"Claesson-Welsh et al." following "Proc. Natl. Acad. Sci." insert -- USA, --.
"Escobedo et al.", delete "1998" and substitute therefor -- 1988 --.
"Giese et al." delete "v-esis" and substitute therefor -- v-*sis* --.
"Claesson-Welsh et al." delete "a *Mol. Cell, Biol,*" and substitute therefor -- *Mol. Cel. Biol.*, --.
"King et al." delete "*Sicnece*" and substitute therefor -- *Science* --.

Drawings,
Figure 3-4, add a circle over residue 600.
Figure 3-5, add an asterisk over residue 849.

Column 1,
Line 6, delete "fled" and substitute therefor -- filed --.
Line 7, delete the comma following "07/915,884,".

Column 3,
Line 34, delete "call" and substitute therefor -- called --.
Line 36, delete "disclosure" and substitute therefor -- disclosed --.

Column 4,
Line 11, delete "*subilis*" and substitute therefor -- *subtilis* --.
Line 26, delete "(antagonists" and substitute therefor -- antagonists --.

Column 5,
Line 41, delete "withing" and substitute therefor -- within --.
Line 43, delete "1" and substitute therefor -- a --.

Column 6,
Line 10, delete "in situ" and substitute therefor -- *in situ* --.

Column 8,
Lines 37 and 47, delete "˜3-kbp" and substitute therefor -- ~3-kbp --.

UNITED STATES PATENT AND TRADEMARK OFFICE
CERTIFICATE OF CORRECTION

PATENT NO. : 6,228,600 B1
DATED : May 8, 2001
INVENTOR(S) : Matsui et al.

It is certified that error appears in the above-identified patent and that said Letters Patent is hereby corrected as shown below:

Column 9,
Line 35, delete "Under" and substitute therefor -- under --.

Column 13,
Line 35, delete "∼3-kbp" and substitute therfore -- ~3-kbp --.

Column 14,
Line 3, delete "~3-kbp" and substitute therefor -- ~3-kbp --.

Column 15,
Line 7, delete "in situ" and substitute therefor -- *in situ* --.
Line 14, delete "dentinogenesis imperfecta" and substitute therefor
-- *dentinogenesis imperfecta* --.

Column 16,
Line 23, delete "to" and substitute therefor -- two --.

Column 17,
Line 30, following "at" insert -- least --.

Column 18,
Line 19, delete "32-αR and 32β-R" and substitute therefor -- 32D-αR and 32D-βR --.
Line 21, delete "membranes" and substitute therefor -- membrane --.
Line 24, delete "32D-β" and substitute therefor -- 32D-βR --.

Column 19,
Line 44, delete "wells" and substitute therefor -- well --.

Signed and Sealed this

Tenth Day of September, 2002

*Attest:*

*Attesting Officer*

JAMES E. ROGAN
*Director of the United States Patent and Trademark Office*